United States Patent [19]

Chen

[11] Patent Number: 6,148,830
[45] Date of Patent: Nov. 21, 2000

[54] TEAR RESISTANT, MULTIBLOCK COPOLYMER GELS AND ARTICLES

[75] Inventor: John Y. Chen, Pacifica, Calif.

[73] Assignee: Applied Elastomerics, Inc., South San Francisco, Calif.

[21] Appl. No.: 08/719,817

[22] Filed: Sep. 30, 1996

Related U.S. Application Data

[63] Continuation-in-part of application No. 08/665,343, Jun. 17, 1996, application No. 08/612,586, Mar. 8, 1996, application No. 08/581,125, Dec. 29, 1995, application No. 08/581,191, Dec. 29, 1995, Pat. No. 5,760,117, application No. 08/581,188, Dec. 29, 1995, abandoned, application No. 08/288,690, Aug. 11, 1994, Pat. No. 5,633,286, application No. PCT/US94/07314, Jun. 27, 1994, and application No. PCT/US94/04278, Apr. 19, 1994.

[51] Int. Cl.$^7$ .............................. A61C 15/00; B32B 5/16; B32B 27/08; B32B 27/32

[52] U.S. Cl. .......................... 132/321; 428/407; 428/515; 428/521; 525/959; 524/270; 524/474; 524/476; 524/490; 524/505; 521/148

[58] Field of Search .................................. 428/409, 521, 428/515; 524/270, 474, 476, 490, 505; 2/411; 5/632, 636, 640; 132/321; 135/68, 71; 427/162; 521/148; 525/95; 174/77 R, 92, 93

[56] References Cited

U.S. PATENT DOCUMENTS

| | | | |
|---|---|---|---|
| Re. 27,145 | 6/1971 | Jones | 260/880 |
| 2,993,874 | 7/1961 | Hoel | 260/27 |
| 3,149,182 | 9/1964 | Porter | 260/879 |
| 3,239,476 | 3/1966 | Harlan | 260/27 |
| 3,239,478 | 3/1966 | Harlan | 260/27 |
| 3,265,765 | 8/1966 | Holden | 260/876 |
| 3,325,430 | 6/1967 | Grasley | 260/25 |
| 3,333,024 | 7/1967 | Haefele | 260/880 |
| 3,464,850 | 9/1969 | Haefele | 117/135.5 |
| 3,485,787 | 12/1969 | Haefele | 260/33.6 |
| 3,595,942 | 7/1971 | Wald | 260/880 |
| 3,660,849 | 5/1972 | Jonnes | 2/2.1 |
| 3,821,149 | 6/1974 | Makowski | 260/30.6 |
| 3,827,999 | 8/1974 | Crossland | 260/33.6 |
| 3,860,013 | 1/1975 | Czapor | 132/91 |
| 4,006,116 | 2/1977 | Dominguez | 260/33.6 |
| 4,032,459 | 6/1977 | Crossland | 252/51.5 |

(List continued on next page.)

FOREIGN PATENT DOCUMENTS

| | | |
|---|---|---|
| 146163 | 11/1984 | European Pat. Off. . |
| 285181 | 4/1988 | European Pat. Off. . |
| 439180 | 1/1991 | European Pat. Off. . |
| 483370 | 4/1991 | European Pat. Off. . |
| 1268431 | 3/1972 | Germany . |
| 2019416 | 4/1979 | United Kingdom . |
| WO 88/00603 | 1/1988 | WIPO . |
| WO 90/05166 | 5/1990 | WIPO . |
| WO 91/05014 | 4/1991 | WIPO . |
| WO 93/05113 | 3/1993 | WIPO . |
| WO 93/23472 | 11/1993 | WIPO . |

OTHER PUBLICATIONS

Allen, et al; Comprehensive Polymer Science—vol. 7; 1994; pp. 416–431.

Kirk–Othmer; Encyclopedia of Chemical Technology; 1994; 4$^{th}$ Edition; pp. 17–37.

Garder, William; Gardner's Chemical Synonyms and Trade Names; 1994;.

"Styrene–Diene Triblock Copolymers: Orientation Conditons and Mechanical Properties of the Oriented Materials" A. Weill and R. Pixa, Journal of Polymer Science Polymer Symposium 58, 381–394 (1977).

Septon Trade Literature, Kuraray Co., Ltd. 1995.8 (4,000) 15 pages,

SC:1102–89 Shell Chemical Technical Bulletin"KRATON® Thermoplastic Rubber in Oil Gels", Apt. 1989.

Septon, High Performance Thermoplastic Rubber, Kurraray Co., Ltd., 1995.

Kraton Polymers, May 1997, Shell Chemical Company.

Silipos manual, Advanced Polymer Technology; Niagara Falls, NY. 14307, 1994.

Melt Miscibility in Blends of Polypropylene, Polystryenhe–Block–Poly(Ethylene–Sat–Butylene)–Block–Polystyrene, And Processing Oil From Melting Point Depression, Ohlesson et al., Polymer Engineering and Science, 1996, vol. 36, No. 11.

Blends And Thermoplastic Interpenetrating Polymer Networks Of Polypropytlene And Polystyrene–Block–Poly-(Ethylene–Stat–Butylene)–Block–Polystyrene Triblock Copolymer. 1: Morphology And Structure–Related Properties, Ohlesson, et al., Polymer Engineering and Science, Feb. 1992, vol. 36, no. 4.

Migration And Blooming Of Waxes To The Surface Of Rubber Vulcanizates, Nah, et al., J. Of Polymer Sci4nce: Polymer Physics Ed., vol. 18, 511–521 (1980).

*Primary Examiner*—Herbert J. Lilling

[57] ABSTRACT

Novel gels and articles are formed from an intimate melt blend admixture of one or more of a linear or star-shaped multiblock copolymers having two or more midblock polymer chains and high levels of a plasticizing oil.

The gels can be transparent and have a novel combination of properties including unexpectedly high elongation and tensile strength and excellent shape retention after extreme deformation under high velocity impact and stress conditions. The gels of this invention are extremely soft, flexible, and have elastic memory, characterized by a gel rigidity of from about less than 2 gram to about 1,800 gram Bloom and higher. These and other properties are particularly essential for the gels to have utility as composites, toys, therapeutic hand excercising grips, electrical and electronic encapsulation, shock absorbers, acoustical isolators, components for cushions, medical, sports medical, and many other uses. The gels are characterized by a rigidity of about 350 grams to about 1,800 gram Bloom, a tear resistance of at least about 1 Kg/cm, and strands of the gel are capable of flossing at least ten cycles without completely breaking apart as tested under fully contacting surfaces under a uniform spring load of 0.9027 Kg.

20 Claims, 2 Drawing Sheets

U.S. PATENT DOCUMENTS

| | | | |
|---|---|---|---|
| 4,036,910 | 7/1977 | Anderson | 528/338 |
| 4,039,629 | 8/1977 | Himes | 260/880 |
| 4,041,103 | 8/1977 | Davison | 260/857 |
| 4,080,348 | 3/1978 | Korpman | 260/27 |
| 4,136,071 | 1/1979 | Korpman | 260/27 |
| 4,136,699 | 1/1979 | Collins | 128/290 |
| 4,151,057 | 4/1979 | St. Clair . | |
| 4,176,240 | 11/1979 | Sabia | 174/23 |
| 4,259,540 | 3/1981 | Sabia . | |
| 4,313,867 | 2/1982 | Duvdevani | 260/33.6 |
| 4,351,913 | 9/1982 | Patel . | |
| 4,361,508 | 11/1982 | Bourland | 523/173 |
| 4,369,284 | 1/1983 | Chen . | |
| 4,432,607 | 2/1984 | Levy | 350/96.34 |
| 4,481,323 | 11/1984 | Sterling | 524/269 |
| 4,492,428 | 1/1985 | Levy . | |
| 4,497,538 | 2/1985 | Patel . | |
| 4,509,821 | 4/1985 | Stenger | 350/96.23 |
| 4,511,354 | 4/1985 | Sterling | 604/98 |
| 4,600,261 | 7/1986 | Debbaut . | |
| 4,610,738 | 9/1986 | Jervis | 156/49 |
| 4,618,213 | 10/1986 | Chen . | |
| 4,643,924 | 2/1987 | Uken | 428/35 |
| 4,662,692 | 5/1987 | Uken | 339/96 |
| 4,678,664 | 7/1987 | Schmolka | 424/65 |
| 4,680,233 | 7/1987 | Camin | 428/424.6 |
| 4,690,831 | 9/1987 | Uken | 427/44 |
| 4,692,369 | 9/1987 | Nomi | 428/198 |
| 4,709,982 | 12/1987 | Corne | 427/44 |
| 4,716,183 | 12/1987 | Gamarra | 522/90 |
| 4,721,832 | 1/1988 | Toy | 174/87 |
| 4,764,535 | 8/1988 | Leicht . | |
| 4,798,853 | 1/1989 | Handlin | 523/173 |
| 4,801,346 | 1/1989 | Huddleston . | |
| 4,822,834 | 4/1989 | Blevins | 524/427 |
| 4,833,193 | 5/1989 | Sieverding . | |
| 4,842,931 | 6/1989 | Zook | 428/354 |
| 4,864,725 | 9/1989 | Debbaut | 429/871 |
| 4,865,905 | 9/1989 | Uken | 428/220 |
| 4,880,676 | 11/1989 | Pulgcerver | 428/35.7 |
| 4,880,878 | 11/1989 | Himes | 528/89 |
| 4,883,431 | 11/1989 | Uken . | |
| 4,888,070 | 12/1989 | Clark . | |
| 4,889,171 | 12/1989 | Covington | 428/304 |
| 4,889,403 | 12/1989 | Zucker . | |
| 4,900,877 | 2/1990 | Dubrow | 174/35 |
| 4,909,756 | 3/1990 | Jervis . | |
| 4,929,211 | 5/1990 | Resnick | 446/14 |
| 4,942,270 | 7/1990 | Gamarra | 174/93 |
| 4,944,363 | 7/1990 | Osher | 273/58 |
| 4,944,973 | 7/1990 | Follette . | |
| 4,968,747 | 11/1990 | Mallikarjun | 525/74 |
| 4,983,008 | 1/1991 | Campbell | 350/96.16 |
| 5,026,054 | 6/1991 | Osher | 273/58 |
| 5,059,748 | 10/1991 | Allen | 174/87 |
| 5,068,138 | 11/1991 | Mitchell | 428/36.8 |
| 5,085,597 | 2/1992 | Story | 439/521 |
| 5,088,734 | 2/1992 | Glava | 273/73 |
| 5,098,421 | 3/1992 | Zook | 604/367 |
| 5,112,900 | 5/1992 | Buddenhagen | 524/484 |
| 5,126,182 | 6/1992 | Douglas | 428/90 |
| 5,149,736 | 9/1992 | Gamarra | 524/490 |
| 5,153,254 | 10/1992 | Chen | 524/505 |
| 5,159,022 | 10/1992 | Ikematu | 525/250 |
| 5,167,649 | 12/1992 | Zook | 604/307 |
| 5,173,573 | 12/1992 | Jervis | 174/138 |
| 5,177,143 | 1/1993 | Toy | 524/848 |
| 5,181,914 | 1/1993 | Zook | 604/307 |
| 5,191,752 | 3/1993 | Murphy | 54/44.5 |
| 5,221,534 | 6/1993 | Deslauriers | 424/78.03 |
| 5,239,723 | 8/1993 | Chen | 15/104 |
| 5,262,468 | 11/1993 | Chen | 524/476 |
| 5,313,019 | 5/1994 | Brusselmans et al. | 174/93 |
| 5,324,222 | 6/1994 | Chen | 446/34 |
| 5,330,452 | 7/1994 | Zook | 604/307 |
| 5,334,646 | 8/1994 | Chen | 524/474 |
| 5,336,708 | 8/1994 | Chen | 524/505 |
| 5,442,004 | 8/1995 | Sutherland | 524/140 |
| 5,459,193 | 10/1995 | Anderson | 524/505 |
| 5,475,890 | 12/1995 | Chen | 15/104 |
| 5,479,952 | 1/1996 | Zachariades | 132/321 |
| 5,541,250 | 7/1996 | Hudson | 524/505 |
| 5,559,165 | 9/1996 | Paul | 523/111 |
| 5,580,572 | 12/1996 | Mikler | 424/448 |
| 5,606,149 | 2/1997 | Yaworski | 174/92 |
| 5,618,882 | 4/1997 | Hammond | 525/92 |
| 5,624,294 | 4/1997 | Chen | 446/253 |
| 5,626,657 | 5/1997 | Pearce | 106/122 |
| 5,633,286 | 5/1997 | Chen | 524/474 |
| 5,655,947 | 8/1997 | Chen | 446/46- |

| | |
|---|---|
| M1 | Fabric or Cloth |
| G | Gel |
| GM | Gel-Sponge or Gel-Foam |
| M2 | Foam or Sponge |
| M3 | Synthetic Resin or Plastic |
| M4 | Fibre |
| M5 | Concrete |
| M6 | Metal or Metal Sponge |
| M7 | Wood |
| M8 | Wire or Screening |
| M9 | Refractory Material |
| M10 | Other Material |

TEAR RESISTANT, MULTIBLOCK COPOLYMER GELS AND ARTICLES

ORIGINS OF INVENTION AND RELATED APPLICATIONS

This application is a CIP of Ser. No. 08/665,343 filed Jun. 17, 1996 and a CIP of Ser. No. 08/612,586 filed Mar. 8, 1996 and a CIP of 08/581,125 filed Dec. 29, 1995 and also a CIP of 08/581,191 filed Dec. 29, 1995, now U.S. Pat. No. 5,760,117. This application is also a CIP of Ser. No. 08/581, 188 filed Dec. 29, 1995 now abandoned and a CIP of Ser. No. 08/288,690 filed Aug. 11, 1994, now U.S. Pat. No. 5,633,286 and also a CIP of PCT/US94/07314 filed Jun. 27, 1994 and a CIP of PCT/US94/04278 filed Apr. 19, 1994.

FIELD OF THE INVENTION

The present invention relates to gels and gel articles.

BACKGROUND OF THE INVENTION

This application is based upon subject matters described in earlier filed and copending related applications and patents (see Related Applications above) which are specifically incorporated herein by reference.

A general view of oriented block copolymers is described in a publication by A. Weill and R. Pixa, in Journal of Polymer Science Symposium, 58, 381–394 (1977), titled "Styrene-diene Triblock Copolymers: Orientation Conditions and Mechanical Properties of the Oriented Materials" describe techniques of orientation of neat SIS and SBS block copolymers and their properties.

Other subject matters of interest are:

Elastomeric Thermoplastic, Vol. 5, pages 416–430; Block Copolymers, Vol. 2, pages 324; Block and Graft Copolymers; Styrene-Diene Block Copolymers, Vol. 15, pages 508–530; and Microphase Structure, can be found in *ENCYCLOPEDIA OF POLYMER SCIENCE AND ENGINEERING*, 1987.

Legge, N. R., et al., Chemistry and Technology of Block Polymers, Ch. 29, pages 394–429, ACS, Organic Coatings and Plastics Chemistry,© 1975.

Legge, N. R., Thermoplastic Elastomers, Rubber Chemistry and Technology, Vol. 60, pages G79–117.

Lindsay, G. A., et al., Morphology of Low Density Polyethylene/EPDM Blends Having Tensile Strength Synergism, source: unknown.

Cowie, J. M. G., et al., Effect of Casting on the Stress-Hardening and Stress-Softening Characteristics of Kraton-G 1650 Copolymer Films, J. Macromol. Sci.-Phys., B16(4), 611–632 (1979).

Futamura, S., et al., Effects of Center Block Structure on the Physical and Rheological Properties of ABA Block Copolymers. Part II. Rheological Properties, Polymer Engineering and Science, August, 1977, Vol. 17, No. 8, pages 563–569.

Kuraray Co., LTD. MSDS, Kuraray Septon 4055, Hydrogenated Styrene Isoprene/Butadiene Block Copolymer, Apr. 25, 1991.

SUMMARY OF THE INVENTION

The invention comprises gels and articles made from multiblock copolymers having two or more midblock polymer chains which gels exhibit advantages of improved tear propagation resistance. The gels also possess high tensile strength and rapid return from high extension and can exist in an altered state of delay elastomeric recovery as it regains its original shape following high extensions or dynamic deformations. Such combination of properties are not found in gels of substantially the same rigidity made from triblock copolymers. The gels of the present invention also exhibit low set, high dimensional stability, crack, tear, craze, and creep resistance, excellent tensile strength and high elongation, long dynamic shear, tear and stress forces, excellent processing ability for cast molding, extruding, fiber forming film forming and spinning, non-toxic, nearly tasteless and odorless, soft and strong, optically clear, highly flexible, processing elastic memory, substantially with little or no plasticizer bleedout. The gels are especially suitable and have advantages where resistance to dynamic stretching, shearing and tearing forces are particularly critical such as those forces acting during dental flossing, while gels in the altered state with delay elastomeric recovery from deformation and extension are excellent for use where energy and vibration damping at high impact, low frequencies, such as in running shoe cushioning designs are essential.

Moreover, the gels can be made with selectively lower gel rigidities while achieving higher tensile strength or can be orientated to achieve high gel rigidities with lower gel tensile strengths.

Generally, the unique tear resistant gels comprises: (I) 100 parts by weight of one or more of a crystalline linear or star-shaped multiblock copolymers or a mixture of two or more of said copolymers; said linear multiblock copolymer have the general configuration A—Z—A and said star-shaped multiblock copolymer have the general configuration (A—Z)n, the subscript n being a number and in the case n is the interger 2, $(A—Z)_2$ denotes simply A—Z—A; wherein each A is a selected glassy polymer end block segment of polystyrene, poly(alpha-methylstyrene), poly(o-methylstyrene), poly(m-methylstyrene), poly(p-methylstyrene) or poly(tertiary-butylstyrene) and wherein Z is a midblock of one or more polymer chains of crystalline forming poly(ethylene) in combination with one or more polymer chains of poly(ethylene-butylene) or poly(ethylene-propylene); said multiblock copolymers optionally in combination with or without a selected amount of one or more of a (II) polymer or copolymer, and selected amounts of a plasticized oil (III) sufficient to achieve gel rigidities of from less than about 2 gram Bloom to about 1,800 gram Bloom and higher.

In another embodiment of the invention, the gels can also be made into composites comprising: (i) one or more of a crystalline midblock linear or star-shaped multiblock copolymers with glassy polymer end blocks or a mixture of two or more of said copolymers; said copolymers having two or more midblock polymer chains and (ii) a selected amount of a plasticizing oil; (iii) said gel, denoted by G, is physically interlocked with a selected material M forming said gel composite of the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, or a permutation of one or more of said $G_n$ with $M_n$, wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity; wherein said gel is capable of exhibiting greater tear propagation resistance than a gel having a corresponding rigidity made from poly(styrene-ethylene-butylene-styrene) or poly(styreneethylene-propylene-styrene) block copolymers having substantially non-crystalline forming poly(ethylene) midblocks.

The linear and star-shaped multiblock copolymers comprises one or more of a crystalline midblock polymer with glassy end block ($A^n$) of a monoalkenyl arene compounds, more specifically, a monovinyl aromatic compounds, and midblocks (Z) comprising two or more segment polymer chains of poly(ethylene), poly(butylene), poly(propylene), poly(ethylene-butylene), and poly(ethylene-propylene).

The (I) linear copolymers are characterized as having a Brookfield Viscosity value at 5 weight percent solids solution in toluene at 30° C. of from less than about 40 cps to about 150 cps and higher, advantageously from about 40 cps to about 60 cps and higher, more advantageously from about 50 cps to about 80 cps and higher, still more advantageously from about 70 cps to about 110 cps and higher, and even more advantageously from about 90 cps to about 180 cps and higher.

The (I) star-shaped copolymers are characterized as having a Brookfield Viscosity value at 5 weight percent solids solution in toluene at 30° C. of from about 150 cps to about 380 cps and higher, advantageously from about 150 cps to about 260 cps and higher, more advantageously from about 200 cps to about 580 cps and higher, and still more advantageously from about 500 cps to about 1,000 cps and higher.

As used herein, the term "gel rigidity" in gram Bloom is determined by the gram weight required to depress a gel a distance of 4 mm with a piston having a cross-sectional area of 1 square centimeter at 23° C.

The various aspects and advantages will become apparent to those skilled in the art upon consideration of the accompanying disclosure.

DESCRIPTION OF THE DRAWINGS

FIGS. 2(a–d). Representative sectional views of composite gel articles of the invention (FIG. 2a=MGM, FIG. 2b=GMG, FIG. 2C=MGMGMGM, FIG. 2D=porous substrate such as foam, fabric, etc. entirely interlocked with gel).

DESCRIPTION OF THE INVENTION

The gels of the invention comprises high viscosity linear multiblock copolymers and star-shaped (or radial) multiblock copolymers having the general configurations $A^n$—Z—$A^n$ and $(A^n—Z)_n$ wherein each $A^n$ is a selected crystalline midblock polymer with glassy end block of a monoalkenyl arene compounds, more specifically, a monovinyl aromatic compounds such as polystyrene (where superscript n=1), monovinylnaphithalene as well as the alkylated derivatives thereof such as poly(alpha-methylstyrene) (n=2), poly(o-methylstyrene) (n=3), poly(m-methylstyrene) (n=4), poly(p-methylstyrene) (n=5) poly (tertiary-butylstyrene) (n=6), and the like, and midblocks (Z) comprising two or more polymer chains of poly(ethylene), poly(butylene) or poly(propylene) in combination with one or more polymer chains of poly(ethylene-butylene) or poly (ethylene-propylene). The subscript n being a number and when subscript n is the integer 2, $(A^nZ)_2$ denotes simply $A^n$—Z—$A^n$. These are denoted by (E), (B), (P), (EB), and (EP) respectively.

The midblock components (Z) can comprise various combinations of midblocks between the selected end blocks (A); these include:

—E—EB—, —E—EP—, —B—EP—, —B—EB—, —E—EP—E—, —E—EB—E—, —B—EP—E—, —B—EB—E—, —B—EP—B—, —B—EB—B—, —E—E—EP—, —E—E—EB—, —B—E—EP—, —B—E—EB—, —B—B—EP—, —B—B—EB—, —E—B—EB—, —E—B—EP—, —EB—EP—, —EB—EB—, —EP—EP—, —E—EB—EB—, —E—EP—EP—, —E—EB—EP—, —E—EP—EB—, —B—EB—EB—, —B—EP—EP—, —B—EB—EP—, —B—EP—EB—, —E—EP—E—EP—, —E—EB—E—EB—, —E—EP—E—EB—, —B—EP—B—EP—, —B—EB—B—EB, —B—EB—B—EP—, —B—EB—E—EB—, —B—EP—E—EP—, —E—EB—B—EP—, —E—EP—B—EB—, —P—EB—, —P—EP—, —P—EP—P—, —P—EB—P—, —B—EP—P—, —B—EB—P—, —P—E—EP—, —P—E—EB—, —B—P—EP—, —B—P—EB—, —P—B—EB—, —P—B—EP—, —P—EB—EB—, —P—EP—EP—, —P—EB—EP—, —P—EP—EB—, —P—EP—P—EP—, —P—EB—P—EB—, —P—EP—P—EB—, —B—EB—P—EB—, —B—EP—P—EP—, —P—EB—B—EP—, —P—EP—B—EB—, —E—EP—P—, —E—EB—P—, —E—P—EP—, —E—P—EB—, —E—EP—P—EP—, —E—EB—P—EB—, —E—EP—P—EB—, —E—EP—E—EP—E—, —B—EP—B—EP—B—, —P—EP—P—EP—P—, —E—EB—E—EB—E—, —P—EP—P—EP—P—, and the like.

The (Z) midblock of two or more polymer chains can be obtained by hydrogenation methods, for example: 1,4-polybutadiene ($B_{1,4}$) can be converted by hydrogenation to poly(ethylene), 1,4-polybutadiene ($B_{1,4}$) and 1,2-polybutadiene ($B_{1,2}$) can be converted by hydrogenation to poly(ethylene-butylene), 1,4-polyisoprene ($I_{1,4}$) can be converted by hydrogenation to poly(ethylene-propylene), 1,2-polybutadiene ($B_{1,2}$) can be converted by hydrogenation to atactic poly(1-butene) (polybutylene), 1,4-polybutadiene ($B_{1,4}$) and polyisoprene (I) 1,4-polybutadiene ($B_{1,4}$) can be converted by hydrogenation to poly(ethylene-ethylene-co-propylene-ethylene), 2-methyl-1,3-polybutadiene, and 1,3-polybutadiene (I, $B_{1,3}$) can be converted by hydrogenation to poly(ethylene-ethylene-co-propylene), and the like. Polypropylene can be modified by tailblocking a poly (ethylene-propylene) copolymer segment on the propylene block to form poly(propylene-ethylene-co-propylene); likewise, poly(ethylene-propylene)$_n$ (EP), poly(propylene-ethylene-co-propylene-propylene) (P—EP—P), poly (propylene-ethylene-propylene) (P—E—P), poly(ethylene-ethylene-co-propylene) (E—EP) can be formed. It is noted herein that B (bold) denotes polybutadiene and B (plain) denotes polybutylene.

Further, the multiblock copolymers ($A^n$—Z—$A^n$) can be obtained by various synthesis methods including hydrogenation of selected block copolymers. When the Superscript n of A is=1, (polystyrene) (S), for example, suitable block copolymers can be converted to the useful multiblock copolymers forming the gels. These include: conversions of S—I—$B_{1,3}$—S to (S—E—EP—S), S—$B_{1,4}$—I—$B_{1,4}$—S to (S—E—EP—E—S), S—$B_{1,2}$—I—S to (S—B—EP—S), (S—$B_{1,3}$—$B_{1,2}$—$B_{1,4}$—S to (S—E—EB—S), S—$B_{1,4}$—$B_{1,2}$—I—S to (S—EB—EP—S), S—I—$B_{1,3}$—$B_{1,2}$—$B_{1,4}$—S to (S—E—EP—EB—S), etc. As denoted herein abbreviations are interchangeably used, for example, (S—E—EP—S) denotes poly(styrene-ethylene-ethylene-co-propylene-styrene). Other linear multiblock copolymers (denoted in abbreviations) can be formed, including:

(S—B—EB—S), (S—E—EB—E—S), (S—B—EP—E—S), (S—B—EB—E—S), (S—B—EP—B—S), (S—B—

EB—B—S), (S—E—E—EP—S), (S—E—E—EB—S), (S—B—E—EP—S), (S—B—E—EB—S), (S—B—B—EP—S), (S—B—B—EB—S), (S—E—B—EB—S), (S—E—B—EP—S), (S—EB—EB—S), (S—EP—EP—S), (S—E—EB—EB—S), (S—E—EP—EP—S), (S—E—EB—EP—S), (S—B—EB—EB—S), (S—B—EP—EP—S), (S—B—EB—EP—S), (S—B—EP—EB—S), (S—E—EP—E—EP—S), (S—E—EB—E—EB—S), (S—E—EP—E—EB—S), (S—B—EP—B—EP—S), (S—B—EB—B—EB—S), (S—B—EB—B—EP—S), (S—B—EB—E—EB—S), (S—B—EP—E—EP—S), (S—E—EB—B—EP—S), (S—E—EP—B—EB—S), (S—P—EB—S), (S—P—EP—S), (S—P—EP—P—S), (S—P—EB—P—S), (S—B—EP—P—S), (S—B—EB—P—S), (S—P—E—EP—S), (S—P—E—EB—S), (S—B—P—EP—S), (S—B—P—EB—S), (S—P—B—EB—S), (S—P—B—EP—S), (S—P—EB—EB—S), (S—P—EP—EP—S), (S—P—EB—EP—S), (S—P—EP—EB—S), (S—P—EP—P—EP—S), (S—P—EB—P—EB—S), (S—P—EP—P—EB—S), (S—B—EB—P—EB—S), (S—B—EP—P—EP—S), (S—P—EB—B—EP—S), (S—P—EP—B—EB—S), (S—E—EP—P—S), (S—E—EB—P—S), (S—E—P—EP—S), (S—E—P—EB—S), (S—E—EP—P—EP—S), (S—E—EB—P—EB—S), (S—E—EP—P—EB—S), (S—E—EP—E—EP—E—S), (S—B—EP—B—EP—B—S), (S—P—EP—P—EP—P—S), (S—E—EB—E—EB—E—S), (S—P—EP—P—EP—P—S), and the like.

The multiblock star-shaped (or radial) copolymers (A$^n$—Z)$_n$ can be obtained by various synthesis methods including hydrogenation of selected block copolymers. When the superscript n of A is=1, (polystyrene) (S), for example, suitable block copolymers can be converted to the useful multiblock copolymers forming the gels. These include: conversions of (S—I—B$_{1,3}$)$_n$ to poly(styrene-ethylene-ethylene-co-propylene)$_n$ denoted by the abbreviation (S—E—EP)$_n$, (S—B$_{1,4}$—I—B$_{1,4}$)$_n$ to (S—E—EP—E)$_n$, (S—B$_{1,2}$—I)$_n$ to (S—B—EP)$_n$, (S—B$_{1,3}$—B$_{1,2}$—B$_{1,4}$)$_n$ to (S—E—EEB)$_n$, (S—B$_{1,4}$—B$_{1,2}$—I)$_n$ to (S—EB—EP)$_n$, (S—I—B$_{1,3}$—B$_{1,2}$—B$_{1,4}$)$_n$ to (S—E—EP—EB)$_n$, etc. Other multiblock copolymers can be formed, including: (S—B—EB)$_n$, (S—E—EB—E)$_n$, (S—B—EP—E)$_n$, (S—B—EB—E)$_n$, (S—B—EP—B)$_n$, (S—B—EB—B)$_n$, (S—E—E—EP)$_n$, (S—E—E—EB)$_n$, (S—B—E—EP)$_n$, (S—B—E—EB)$_n$, (S—B—B—EP)$_n$, (S—B—B—EB)$_n$, (S—E—B—EB)$_n$, (S—E—B—EP)$_m$, (S—EB—EB)$_n$, (S—EP—EP)$_n$, (S—E—EB—EB)$_n$, (S—E—EP—EP)$_n$, (S—E—EB—EP)$_n$, (S—B—EB—EB)$_n$, (S—B—EP—EP)$_n$, (S—B—EB—EP)$_n$, (S—B—EP—EB)$_n$, (S—E—EP—E—EP)$_n$, (S—E—EB—E—EB)$_n$, (S—E—EP—E—EB)$_n$, (S—B—EP—B—EP)$_n$, (S—B—EB—B—EB)$_n$, (S—B—EB—B—EP)$_n$, (S—B—EB—E—EB)$_n$, (S—B—EP—E—EP)$_n$, (S—E—EB—B—EP)$_n$, (S—E—EP—B—EB)$_n$, (S—P—EB)$_n$, (S—P—EP)$_n$, (S—P—EP—P)$_n$, (S—P—EB—P)$_n$, (S—B—EP—P)$_n$, (S—B—EB—P)$_n$, (S—P—E—EP)$_n$, (S—P—E—EB)$_n$, (S—B—P—EP)$_n$, (S—B—P—EB)$_n$, (S—P—B—EP)$_n$, (S—P—EB—EB)$_n$, (S—P—EP—EP)$_n$, (S—P—EB—EP)$_n$, (S—P—EP—P—EP)$_n$, (S—P—EB—P—EB)$_n$, (S—P—EP—P—EB)$_n$, (S—B—EB—P—EB)$_n$, (S—B—EP—P—EP)$_n$, (S—P—EB—B—EP)$_n$, (S—P—EP—B—EB)$_n$, (S—E—EP—P)$_n$, (S—E—P—EP)$_n$, (S—E—P—EB)$_n$, (S—E—EP—P—EP)$_n$, (S—E—EB—P—EB)$_n$, (S—E—EP—E—EP)$_n$, (S—B—EP—B—EP—B)$_n$, (S—P—EP—P—EP—P)$_n$, (S—E—EB—E—EB—E)$_n$, (S—P—EP—P—EP—P)$_n$, and the like.

The Z and A portions of the linear and star-shaped multiblock copolymers are incompatible and form a two or more-phase system consisting of sub-micron glassy domains (A) interconnected by flexible Z chains. These domains serve to crosslink and reinforce the structure. This physical elastomeric network structure is reversible, and heating the polymer above the softening point of the glassy domains temporarily disrupt the structure, which can be restored by lowering the temperature. The disruption of the sub-micron domains due to heating above the softening point forces the glassy domains to open up, unlocking the network structure and flow. Upon cooling below the softening point, the glassy polymers reforms together into sub-micron domains, locking into a network structure once again, resisting flow. It is this unlocking and locking of the network structure on the sub-micron scale with the surfaces of various materials which allows the gel to form interlocking composites with other materials.

Theory notwithstanding, the multiblock copolymer gel properties can be attributed to the additional blocks affecting the separate polymer phases, the additional blocks affecting the heterophase structure, the additional blocks affecting the interfacial regions between phases of the multiblock polymers or the additional blocks forming a separate phase or inducing the formation of additional separate phases. Due to the additional number of midblocks of the copolymers (I), the difference in solubility parameters between (A) and (Z) becomes greater than the solubility parameters differences between (A) and (D) of triblock copolymers, where D denotes the lone midblock polymer chain. Moreover, the presence of additional midblocks of ethylene, propylene, butylene, ethylene-propylene, or ethylene-butylene can contribute to stress-induced crystallization. This may explain why as the viscosity of the multiblock copolymers is increased to a higher level, the appearance of the gels change from crystal clear to more translucent white.

The gels of the present invention resist tearing under tensile loads or dynamic deformation in that when cut or notched, the "crack" made on the gel deep surface does not readily propagate further under dynamic deformation or tensile loads. Unlike triblock copolymer gels, such as (SEBS) and (SEPS) gels which possess high tensile strength and will catastrophically snap apart into two reflective clean smooth surfaces when cut or notched under tensile or dynamic loads. Furthermore, when elongated, the instant gels can exhibit two or more draw plateaus and can possess high tensile strength and rapid return from high extension without noticeable set or deformation. As observed, the gels can be stretched by a first tensile load with uniform deformation to a measured length, upon the application of higher tensile loads, the gel can be further extended without breaking. Upon release, the gel returns immediate to its original shape and any necking quickly disappears. Again, theory notwithstanding, the additional drawing plateaus of the gel can be attributed to yielding of crystalline formations ethylene or propylene components in the gel or yield of induced interfacial regions of concentrated ethylene or propylene between the domains which during extension absorbs the elastic energy. Likewise, the resistance to tear propagation of the instant gels when notched under tensile load can be attributed to yielding of the gel midblock components, yielding of additional phases, or yielding of interfacial regions before rupture or deformation of the (A) domains can take place.

Additionally, shearing, heating or cooling form the molten state can alter the gels' state. Thei nstant gels can be made to exhibit long elastomeric recovery times. Such gels can be used effectively in suppressing low frequency vibrations and for absorbing energy. The unusual properties of the gels can be attribured to altering different phase or interfacial arrangements of the domains of the multiblock copolymers.

It should be noted that when the Z to Z ratios falls substantially below about 30:70, various properties such as elongation, tensile strength, tear resistance and the like can decrease while retaining other desired properties, such as gel rigidity, flexibility, elastic memory.

In general, for these block copolymers, the various measured viscosities of 5, 10, 15, and 20, weight percent solution values in toluene at 30° C. can be extrapolated to a selected concentration. For example, a solution viscosity of a 5 weight percent copolymer solution in toluene can be determined by extrapolation of 10, 15, and 20 weight percent measurements to 5 weight percent concentration.

The Brookfield Viscosities can be measured at various neat polymer concentrations, for example, the selected high viscosity linear multiblock coplymers in (I) can have a typical Brookfield Viscosity value of a 20 weight percent solids solution in toluene at 25° C. of about 1,800 cps and higher, and advantageously about 2,000 cps and higher. Typically, the Brookfield Viscosity values can range from at least about 1,800 to about 16,000 cps and higher. More typically, the Brookfield Viscosity values can range from at least about 1,800 cps to about 40,000 cps and higher. Still more typically, the Brookfield Viscosity values can range from at least about 1,800 cps to about 80,000 cps and higher. Due to structural variations between the multiblock and star-shaped copolymers, the high viscosity star-shaped or radial copolymers, typically, may exhibit a lower Brookfield Viscosity value than its counterpart linear multiblock copolymers. However, when the multiblock copolymers are considered as star-shaped or branched, then at equal branch lengths, the solution viscosities of the multiblock copolymers and branched copolymers are about the same or equivalent.

In all cases, the molecular chain lengths (molecular weights) of the multiblock and star-shaped (or radial) copolymers (I) must be sufficient to meet the high solution Brookfield Viscosities requirements described herein that is necessary for making the soft, strong and extreme tear resistant gels.

The copolymers (I) selected have Brookfield Viscosity values ranging from about 1,800 cps to about 80,000 cps and higher when measured at 20 weight percent measured at 25 weight percent solids solution toluene. Typical examples of Brookfield Viscosity values for star-shaped copolymers at 25 weight percent solids solution in toluene at 25° C. can range from about 3,500 cps to about 30,000 cps and higher; more typically, about 9,000 cps and higher. Other advantageous multiblock and multiblock star-shaped copolymers can exhibit viscosities (as measured with a Brookfield model RVT viscometer at 25° C.) at 10 weight percent solution in toluene of about 400 cps and higher and at 15 weight percent solution in toluene of about 5,600 cps and higher. Other advantageous multiblock and star-shaped copolymers can exhibit about 8,000 to about 20,000 cps at 20 weight percent solids solution in toluene at 25° C. Examples of most advantageous high viscosity linear multiblock copolymers can have Brookfield viscosities at 5 weight percent solution in toluene at 30° C. of from about 40 to about 50, 60, 70, 80, 90, 100 . . . 120, 150, 200 cps and higher, while viscosities of star-shaped multiblock copolymers are 150 cps and higher.

Examples of high viscosity multiblock copolymers (I) having two or more midblocks are hydrogenated styrene isoprene/butadiene block copolymers, more specifically, hydrogenated styrene block polymer with 2-methyl-1,3-butadiene and 1,3-butadiene: Kuraray's 4055 (S—E—EP—S) multiblock copolymer and 4077 which exhibit viscosities at 5 weight percent solution in toluene at 30° C. of about 90 cps to about 120 cps and about 200 to about 380 cps respectively. At 10 weight percent 4055 is about 5,800 cps and higher. Other linear and star multiblock copolymers (I) such as (S—E—EP—S), (S—E—EP—E—S), (S—B—EP—S), (S—E—EB—S), (S—EB—EP—S), (S—E—EP—EB—S), (S—B—EB—S), (S—E—EB—E—S), (S—B—EP—E—S), (S—B—EB—E—S), (S—B—EP—B—S), (S—B—EB—B—S), (S—E—E—EP—S), (S—E—E—EB—S), (S—B—E—EP—S), (S—B—E—EB—S), (S—B—B—EP—S), (S—B—B—EB—S), (S—E—B—EB—S), (S—E—B—EP—S), (S—EB—EB—S), (S—EP—EP—S), (S—E—EB—EB—S), (S—E—EP—EP—S), (S—E—EB—EP—S), (S—B—EB—EB—S), (S—B—EP—EP—S), (S—B—EB—EP—S), (S—B—EP—EB—S), (S—E—EP—E—EP—S), (S—E—EB—E—EB—S), (S—E—EP—E—EB—S), (S—B—EP—B—EP—S), (S—B—EB—B—EB—S), (S—B—EP—B—EB—S), (S—B—EB—E—EB—S), (S—B—EP—E—EP—S), (S—P—EB—P—S), (S—B—EP—P—S), (S—B—EB—P—S), (S—P—E—EP—S), (S—P—E—EB—S), (S—B—P—EP—S), (S—B—P—EB—S), (S—P—B—EB—S), (S—P—B—EP—S), (S—P—EB—EB—S), (S—P—EP—EP—S), (S—P—EB—EP—S), (S—P—EP—EB—S), (S—P—EP—P—EP—S), (S—P—EB—P—EB—S), (S—P—EP—P—EB—S), (S—B—EB—P—EB—S), (S—B—EP—P—EP—S), (S—E—EB—P—EB—S), (S—B—EP—B—EB—S), (S—E—EP—P—S), (S—E—EB—P—S), (S—E—P—EP—S), (S—E—P—EB—S), (S—E—EP—P—EP—S), (S—E—EB—P—EB—S), (S—E—EP—P—EB—S), (S—E—EP—E—EP—E—S), (S—B—EP—B—EP—B—S), (S—P—EP—P—EP—P—S), (S—E—EB—E—EB—E—S), (S—P—EP—P—EP—P—S), (S—E—EP)$_n$, (S—E—EP—E)$_n$, (S—B—EP)$_n$, (S—E—EB—S)$_n$, (S—EB—EP—)$_n$, (S—E—EP—EB)$_n$, (S—B—EB)$_n$, (S—E—EB—E)$_n$, (S—B—EP—E)$_n$, (S—B—EB—E)$_n$, (S—B—EP—B)$_n$, (S—B—EB—B)$_n$, (S—E—E—EP)$_n$, (S—E—E—EB)$_n$, (S—B—E—EP)$_n$, (S—B—E—EB)$_n$, (S—B—B—EP)$_n$, (S—B—B—EB)$_n$, (S—E—B—EB)$_n$, (S—E—B—EP)$_n$, (S—EB—EB)$_n$, (S—EP—EP)$_n$, (S—E—EB—EB)$_n$, (S—E—EP—EP)$_n$, (S—E—EB—EP)$_n$, (S—B—EB—EB)$_n$, (S—B—EP—EP)$_n$, (S—B—EB—EP)$_n$, (S—B—EP—EB)$_n$, (S—B—EP—EB)$_n$, (S—E—EP—E—EP)$_n$, (S—E—EB—E—EB)$_n$, (S—E—EP—E—EB)$_n$, (S—B—EP—B—EP)$_n$, (S—B—EB—B—EB)$_n$, (S—B—EB—B—EP)$_n$, (S—B—EB—E—EB)$_n$, (S—B—EP—E—EP)$_n$, (S—E—EB—B—EP)$_n$, (S—E—EP—B—EB)$_n$, (S—P—EB)$_n$, (S—P—EP)$_n$, (S—P—EP—P)$_n$, (S—P—EB—P)$_n$, (S—B—EP—P)$_n$, (S—B—EB—P)$_n$, (S—P—E—EP)$_n$, (S—P—E—EB)$_n$, (S—B—P—EP)$_n$, (S—B—P—EB)$_n$, (S—P—B—EB)$_n$, (S—P—B—EP)$_n$, (S—P—EB—EB)$_n$,(S—P—EP—EP)$_n$, (S—P—EB—EP)$_n$, (S—P—EP—EB)$_n$, (S—P—EP—P—EP)$_n$, (S—P—EB—P—EB)$_n$, (S—P—EP—P—EB)$_n$, (S—B—EB—P—EB)$_n$, (S—B—EP—P—EP)$_n$, (S—P—EB—B—EP)$_n$, (S—P—EP—B—EB)$_n$, (S—E—EP—P)$_n$, (S—E—EB—P)$_n$, (S—E—P—EP)$_n$, (S—E—P—EB)$_n$, (S—E—EP—P—EP)$_n$, (S—E—EB—P—EB)$_n$, (S—E—EP—P—EB)$_n$, (S—E—EP—E—EP—E)$_n$, (S—B—EP—B—EP—B)$_n$, (S—P—EP—P—EP—P)$_n$, (S—E—EB—E—EB—E)$_n$, and (S—P—EP—P—EP—P)$_n$ can also exhibit viscosities at 5 weight percent solution in toluene at 30° C. of from less than about 100 to about 200, 300, 400, 500, 600, 700, 800, 900, 1,000, 1,200, 1,300, 1,600, 1,800, 2,000 cps and higher.

The copolymer (I) forming the gels can have a broad range of A end block to Z center block ratio of about 20:80 or less to about 40:60 or higher. The A:Z weight ratios can range from lower than about 20:80 to above about 40:60 and higher. More specifically, the values can be 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and etc. Other ratio values of less than 19:81 or higher than 51:49 are also possible. Broadly, the styrene block to elastomeric block ratio A:Z of the high viscosity multiblock and star copolymers (I) is about 20:80 to about 40:60 or higher, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 30:70.

The multiblock copolymers (I) such as Kuraray's (S—E—EP—S) 4055 and 4077 while exhibiting a high viscosity also have a lower (30:70) S:E—EP ratio which makes it of advantage in processing the high molecular weight, high viscosity multiblock copolymers into a gel at suitable temperatures.

The gels can optionally comprise selected major or minor amounts of one or more polymers or copolymers (II) provided the amounts and combinations are selected without substantially decreasing the desired properties. The polymers and copolymers can be linear, star-shaped, branched, or multiarm; these including: (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, (SEPS) styrene-ethylene-propylene-styrene block copolymers, $(SB)_n$ styrene-butadiene and $(SEB)_n$, $(SEBS)_n$, $(SEP)_n$, $(SI)_n$ styrene-isoprene multi-arm, branched or star-shaped copolymers, polyethyleneoxide (EO), poly(dimethylphenylene oxide) and the like. Still, other (II) polymers include homopolymers which can be utilized in minor amounts; these include: polystyrene, polybutylene, polyethylene, polypropylene and the like. The conventional term "major" means about 51 weight percent and higher and the term "minor" means 49 weight percent and lower.

Example of (II) polymers, copolymers, and blends include: (a) Kraton G 1651, G 1654X; (b) Kraton G 4600; (c) Kraton G 4609; other suitable high viscosity polymer and oil s include: (d) Tuftec H 1051; (e) Tuftec H 1041; (f) Tuftec H 1052; (g) Kuraray SEEPS 4033 (hydrogenated styrene isoprene/butadiene block copolymers, more specifically, hydrogenated styrene block polymer with 2-methyl-1,3-butadiene and 1,3-butadiene); (h) Kuraray SEBS 8066; (i) Kuraray SEPS 2005; (j) Kuraray SEPS 2006, and (k) blends (polyblends) of (a)–(h) with other polymers and copolymers include: (1) SEBS-SBS; (2) SEBS-SIS; (3) SEBS-(SEP); (4) SEBS-$(SEB)_n$; (5) SEBS-$(SEB)_n$; (6) SEBS-$(SEP)_n$; (7) SEBS-$(SI)_n$; (8) (SEBS-(SI) multiarm; (9) SEBS-$(SEB)_n$; (10) $(SEB)_n$ star-shaped copolymer; (11) s made from blends of (a)–(k) with other homopolymers include: (12) SEBS/polystyrene; (13) SEBS/polybutylene; (14) SEBS/polyethylene; (14) SEBS/polypropylene; (16) SEP/SEBS, (17) SEP/SEPS, (18) SEP/SEPS/SEB, (19) SEPS/SEBS/SEP, (20), SEB/SEBS (21), EB-EP/SEBS (22), SEBS/EB (23), SEBS/EP (24), (25) $(SEB)_n$ s, (26) $(SEP)_n$, (27) Kuraray 2007 (SEPS), (28) Kuraray 2002, (SEPS) and the like.

Representative examples of commercial elastomers that can be combined with the multiblock and star-shaped copolymers (I) described above include: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, D3226, D5298, D5999X, D7340, G1654X, G2701, G2703, G2705, G1706, G2721X, G7155, G7430, G7450, G7523X, G7528X, G7680, G7705, G7702X, 7720 G7722X, G7820, G7821X, G7827, G7890X, G7940, FG1901X and FG1921X. Kuraray's SEPS, SEP/SEPS or SEP/SEB/SEPS Nos. 1001, 1050, 2027, 2003, 2006, 2023, 2043, 2063, 2050, 2103, 2104, 2105, 4045, (SEEPS) 8004, 8007, H-VS-3 (S—V—EP—S) and the like. The Brookfield Viscosity of a 5 weight percent solids solution in toluene at 30° C. of 2006 is about 27. Typical Brookfield Viscosities of a 10 weight percent solids solution in toluene at 30° C. of 1001, 1050, 2007, 2063, 2043, 4033, (SEEPS) 2005, 2006, are about 70, 70, 17, 29, 32, 50, 1200, and 1220 respectively. Typical Brookfield Viscosity of a 25 weight percent solids solution in toluene at 25° C. of Kraton D1101, D1116, D1184, D1300X, G1701X, G1702X are about 4000, 9000, 20000, 6000, 50000 and 50000 cps respectively. Typical Brookfield Viscosity of a 10 weight percent solids solution in toluene at 25° C. of G1654X is about 370 cps. The Brookfield Viscosities of a 20 and 30 weight percent solids solution in toluene at 30° C. of H-VS-3 are about 133 cps and 350 cps respectively.

Suitable triblock copolymers (II) and their typical viscosities are further described: styrene-ethylene-butylene-styrene block copolymers (SEBS) available from Shell Chemical Company and Pecten Chemical Company (divisions of Shell Oil Company) under trade designations Kraton G 1651, Kraton G 1654X, Kraton G 4600, Kraton G 4609 and the like. Shell Technical Bulletin SC:1393–92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68–79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity SEBS triblock copolymers includes Kuraray's SEBS 8006 which exhibits a solution viscosity at 5 weight percent at 30° C. of about 51 cps. Kuraray's 2006 SEPS polymer exhibits a viscosity at 20 weight percent solution in toluene at 30° C. of about 78,000 cps, at 5 weight percent of about 27 cps, at 10 weight percent of about 1220 cps, and at 20 weight percent 78,000 cps. Kuraray SEPS 2005 polymer exhibits a viscosity at 5 weight percent solution in toluene at 30° C. of about 28 cps, at 10 weight percent of about 1200 cps, and at 20 weight percent 76,000 cps. Other grades of SEBS, SEPS, $(SEB)_n$, $(SEP)_n$ polymers can also be utilized in the present invention provided such polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's SEBS polymer 8006 the S:EB weight ratio is about 35:65. In the case of Kuraray's 2005 (SEPS), and 2006 (SEPS), the S:EP weight ratios are 20:80 and 35:65 respectively. Much like S:EB ratios of SEBS and (SEB)$_n$, the SEP ratios of very high viscosity SEPS triblock copolymers are about the same and can typically vary as broadly.

The triblock copolymers (II) such as Kraton G 1654X having ratios of 31:69 or higher can be used and do exhibit about the same physical properties in many respects to Kraton G 1651 while Kraton G 1654X with ratios below 31:69 may also be use, but they are less advantageous due to their decrease in the desirable properties of the final gel.

Plasticizers particularly advantageous for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

Examples of representative commercially available plasticizing oils include Amoco® polybutenes, hydrogenated polybutenes, polybutenes with epoxide functionality at one end of polybutene polymer, liquid poly(ethylene/butylene), liquid heter-telechelic polymers of poly(ethylene/butylene/sytrene) with epoxidized polyisoprene and poly(ethylene/butylene) with epoxidized polyisoprene: Example of such polybutenes include: L-14 (320 Mn), L-50 (420 Mn), L-100 (460 Mn), H-15 (560 Mn, H-25 (610 Mn), H-35 (660 Mn), H-50 (750 Mn), H-100 (920 Mn), H-300 (1290 Mn), L-14E (27–37 cst @ 100° F. Viscosity), H-300E (635–690 cst @ 210° F. Viscosity), Actipol E6 (365 Mn), E16 (973 Mn), E23 (1433 Mn), Kraton L-1203, EKP-206, EKP-207, HPVM-2203 and the like. Example of various commercially oils include: ARCO Prime (55, 70, 90, 200, 350, 400 and the like), Duraprime and Tufflo oils (6006, 6016, 6016M, 6026, 6036, 6056, 6206, etc.), other white mineral oils include: Bayol, Bernol, American, Blandol, Drakeol, Ervol, Gloria, Kaydol, Litetek, Lyondell (Duraprime 55, 70, 90, 200, 350, 400, etc.), Marcol, Parol, Peneteck, Primol, Protol, Sontex, and the like.

Generally, plasticizing oils with average molecular weights less than about 200 and greater than about 700 may also be used (e.g. H-300 (1290 Mn)).

Of all the factors, the amount of plasticizing oils can be controlled and adjusted advantageously to obtain substantially higher tear and tensile strength gels. The improvements in tensile strength of the gels are accompanied by corresponding increase in gel rigidity as the amount of plasticizing oils are lowered until the rigidity of the gels becomes much higher than that of the gums which surround the teeth. Although higher tensile strengths can be obtained as the amount of plasticizing oils in the gel approaches zero, the tensile strength of the floss, however, must be maintained at an acceptable gel rigidity (at sufficient high plasticizing oil levels) in order to be as soft as the gums required for flossing. For example, the rigidities of a gel containing 100, 200, or 300 parts by weight of oil is much higher than a gel containing 300, 400, 500, 600, 800, or 900 parts of oil.

These gels can exhibit a larger unit lateral contraction at the same elongation per unit of length as their counterpart parent gels from which the new gels are derived or formed. This property would allow a same unit volume of gel when elongated as its parent to easily wedge between the teeth when flossing. It would seem that a gel having the 1.0 cm$^3$ volume made from a ratio of 100 parts by weight of copolymer and 400 parts plasticizer would have a unique macro volume configurations that is at equilibrium with the plasticizer when is much like a 3-D fingerprint which is uniquely different from any other gel of a different copolymer to plasticizer ratio. Reducing the plasticizer content of a ratio 100:400 gel to a 100:300 ratio of copolymer to plasticizer will decrease the amount of plasticizer, but the original macro volume configurations will remain the same.

Speculative theories not withstanding, configurations may take the form of (1) swiss cheese, (2) sponge, (3) the insides of a loaf of bread, (4) structures liken to ocean brain corals, (5) large structures and small structures forming the 3-D gel volume landscape, (6) the outer heated surface which cools faster than the inner volumes of the gel during its cooling histories may have a patterned crust (rich in A micro-phases) like that of a loaf of bread and the inner volume may have much like 1–5, and (7) the many different possible structures are unlimited and volume landscapes may be interconnected at the macro-level by threads or micro-strands of Z micro-phases.

The amount of plasticizer extracted can advantageously range from less than about 10% by weight to about 90% and higher of the total weight of the plasticizer. More advantageously, the extracted amounts of plasticizer can range from less than about 20% by weight to about 80% by weight of the total plasticizer, and still more advantageously, from about 25% to about 75%. Plasticizing oils contained in the gels can be extracted by any conventional methods, such as solvent extraction, physical extraction, pressure, pressure-heat, heat-solvent, pressure-solvent-heat, vacuum extraction, vacuum-heat extraction, vacuum-pressure extraction, vacuum-heat-pressure extraction, vacuum-solvent extraction, vacuum-heat-solvent-pressure extraction, etc. The solvents selected, should be solvents which do not substantially disrupt the A and Z phases of the (I) copolymers forming the gels. Any solvent which will extract plasticizer from the gel and do not disrupt the A and Z phases can be utilized. Suitable solvents include alcohols, primary, secondary and tertiary alcohols, glycols, etc., examples include methanol, ethanol, tetradecanol, etc. Likewise, the pressures and heat applied to remove the desired amounts of oils should not be sufficient to disrupt the A and Z domains of the (I) copolymers. To form a lower rigidity gel, the simplest method is to subject the gel to heat in a partial vacuum or under higher vacuum for a selected period of time, depending on the amount of plasticizer to be extracted.

The gels can be made non-adhearing, non-sticking, (non-tacky), by incorporating an advantage amount of stearic acid (octadecanoic acid), metal stearates (e.g., calcium stearate, magnesium stearate, zinc stearate, etc.), polyethylene glycol distearate, polypropylene glycol ester or fatty acid, and polytetramethylene oxide glycol disterate, waxes, stearic acid and waxes, metal stearate and waxes, metal stearate and stearic acid. The use of stearic acid alone do not reduce tack. The amount of stearic acid is also important. As an example, ratio of 200 grams stearic acid to 2,000 gram of SEBS (a ratio of 0.1) will result in spotted tack reduction on the surface of the gel. A ratio of 250 to 2,000 will result in spotted crystallized regions on the surface of the gel or spotted tack reduction. A ratio of 300 to 2,000 will result in complete tack reduction with large stearic acid crystallized regions on the surface of the gel. When microcrystalline waxes are incorporated together with stearic acid, the crystallization of stearic acid completely disappears from the surface of the gel. For example excellent result is achieved with 200 grams of stearic acid, 150 grams of microcrystalline wax and 2,000 grams of SEBS. The same excellent results is achieved when SEBS is adjusted to 3,000 grams, 4,000 grams, etc. The same result is achieved with (I) copolymers as well as in combination with polymers (II) such as SEPS, $(SEB)_n$, $(SEP)_n$ polymers.

The gels can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties. Additives useful in the gel of the present invention include: tetrakis[methylene 3,-(3'5'-di-tertbutyl-4"-hydroxyphenyl) propionate]methane, octadecyl 3-(3",5"-di-tert-butyl-4"-hydroxyphenyl)propionate, distearylpentaerythritol-diproprionate, thiodiethylene bis-(3, 5-ter-butyl-4-hydroxy) hydrocinnamate, (1,3,5-trimethyl-2, 4,6-tris[3,5-di-tert-butyl-4-hydroxybenzyl]benzene), 4,4"-methylenebis(2,6-di-tert-butylphenol), stearic acid, oleic acid, stearamide, behenamide, oleamide, erucamide, N,N"-ethylenebisstearamide, N,N"-ethylenebisoleamide, stearyl erucamide, erucyl erucamide, oleyl palmitamide, stearyl stearamide, erucyl stearamide, calcium sterate, other metal sterates, waxes (e.g. polyethylene, polypropylene, microcrystalline, carnauba, paraffin, montan, candelilla, beeswax, ozokerite, ceresine, and the like). The gel can also contain metallic pigments (aluminum and brass flakes), TiO2, mica, fluorescent dyes and pigments, phosphorescent pigments, aluminatrihydrate, antimony oxide, iron oxides (Fe3O4, —Fe2O3, etc.), iron cobalt oxides, chromium dioxide, iron, barium ferrite, strontium ferrite and other inert magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, Publication NMAB-426, National Academy Press (1985) is incorporated herein by reference.

The gels can also be made into composites. The gels can be casted unto various substrates, such as open cell materials, metals, ceramics, glasses, and plastics, elastomers, fluropolymers, expanded fluropolymers, Teflon (TFE, PTFE, PEA, FEP, etc), expanded Teflon, spongy expanded nylon, etc.; the molten gel composition is deformed as it is being cooled. Useful open-cell plastics include: polyamides, polyimides, polyesters, polyisocyanurates, polyisocyanates, polyurethanes, poly (vinyl alcohol), etc. Open-celled plastic (sponges) suitable for use with the compositions are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The gels denoted as "G" can be physically interlocked with a selected material denoted as "M" to form composites as denoted for simplicity by their combinations $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_n$ $G_nM_n$, $G_nM_nG_nG_n$, $G_nG_nM_n$, $G_nM_nG_nM_nM_n$, $M_nG_nM_n$ $G_nM_nG_n$, $G_nG_nM_nM_nG_n$, $G_nG_nM_nG_nM_n$ $G_n$, and the like or any of their permutations of one or more $G_n$ with $M_n$ and the like, wherein when n is a subscript of M, n is the same or different selected from the group consisting of foam, plastic, fabric, metal, concrete, wood, glass, ceramics, synthetic resin, synthetic fibers or refractory materials and the like; wherein when n is a subscript of G, n denotes the same or a different gel rigidity of from about 2 gram to about 1,800 gram Bloom). The gels of the composites are formed from copolymers (I), polymers (II), and plasticizers (III) described above.

Figure 1:
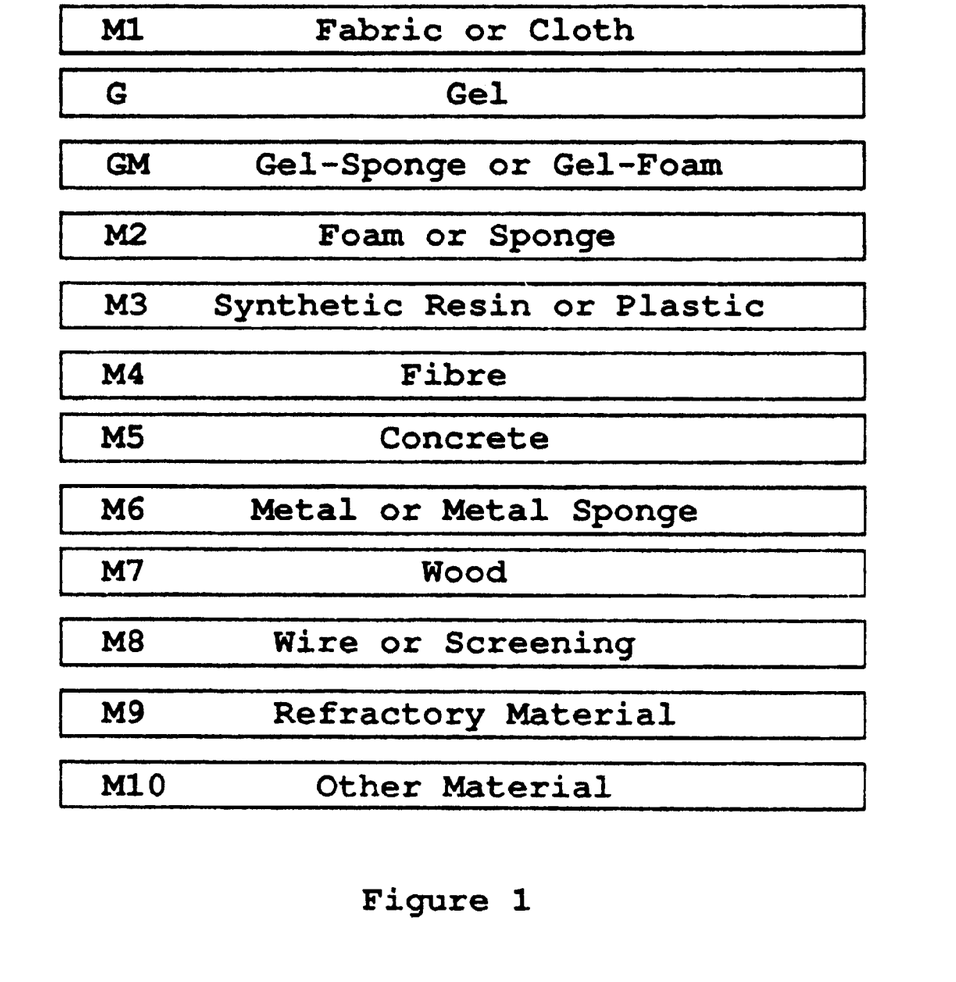
FIG. 1. Representative components materials of composites forming useful articles of the invention.
Figure 2A:
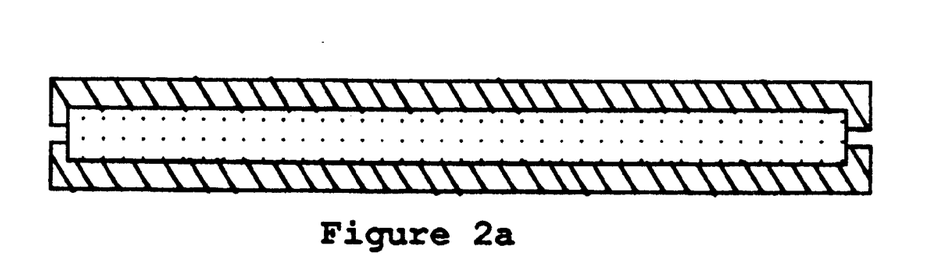
Figure 2B:
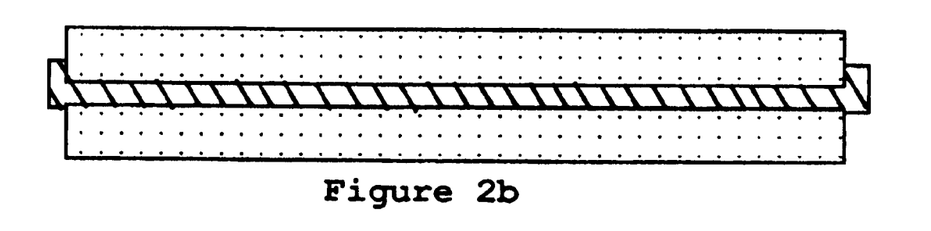
Figure 2C:
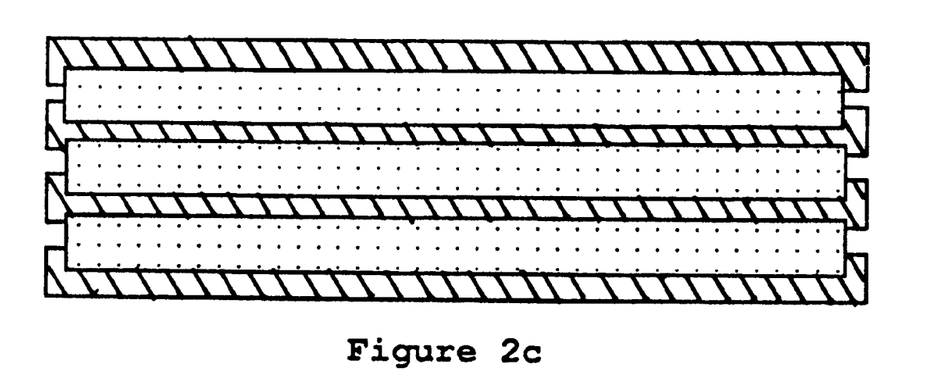
Figure 2D:
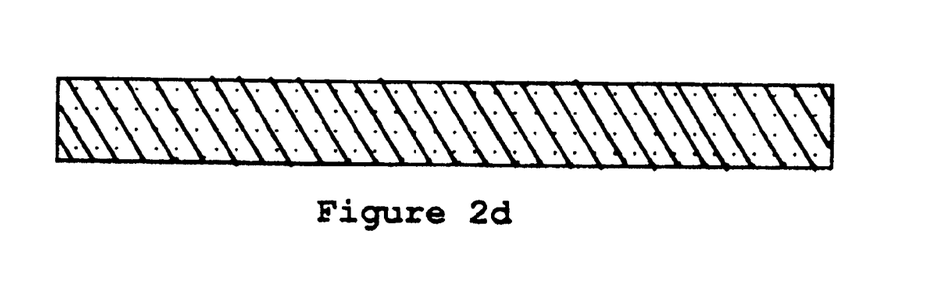

Sandwiches of gel-material (i.e. gel-material-gel or material-gel-material, etc.) are useful as dental floss, shock absorbers, acoustical isolators, vibration dampers, vibration isolators, and wrappers. For example the vibration isolators can be use under research microscopes, office equipment, tables, and the like to remove background vibrations. The tear resistance nature of the instant gels are superior in performance to triblock copolymer gels which are much less resistance to crack propagation caused by long term continue dynamic loadings.

The gels are prepared by blending together the components including other additatives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of multiblock copolymers (I) and polymer (II) used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant compositions in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The gel articles can be formed by blending, injection molding, extruding, spinning, casting and other conventional methods. For example, Shapes having various cross-section can be extruded.

The gels can also be formed directly into articles or remelted in any suitable hot melt applicator and extruded into shaped articles and films or spun into threads, strips, bands, yarns, or other shapes. With respect to various shapes and yarn, its size are conventionally measured in denier (grams/9000 meter), tex (grams/1000 meter), and gage (1/2.54 cm). Gage, tex, denier can be converted as follows: tex=denier/9=specific gravity (2135/gage), for rectangular cross section, tex=specific gravity·(5806×103) (th) (w)/9, where th is the thickness and w the width of the strip, both in centimeters. General descriptions of (1) block copolymers, (2) elastomeric fibers and conventional (3) gels are found in volume 2, starting at pp. 324–415, volume 6, pp 733–755, and volume 7, pp. 515 of *ENCYCLOPEDIA OF POLYMER SCIENCE AND ENGINEERING,* 1987 which volumes are incorporated herein by reference.

The instant gels is excellent for cast molding and the molded products have various excellent characteristics which cannot be anticipated form the properties of the raw components. Other conventional methods of forming the composition can be utilized.

In general, the basis of this invention resides in the fact that one or more of a high viscosity linear multiblock and star-shaped multiblock copolymers (I) or a mixture of two or more of such copolymers having (A) end block to elastomeric block ratio preferably within the contemplated range of styrene to rubber ratios of from about 20:80 to about 40:60 and higher, more preferably from between about 31:69 to about 40:60 and higher when blended in the melt with an appropriate amount of plasticizing oil makes possible the attainment of gels having a desirable combination of physical and mechanical properties, notably high elongation at break of at least 1,600%, ultimate tensile strength of about $8 \times 10^5$ dyne/cm$^2$ and higher, low elongation set at break of substantially not greater than about 2%, tear resistance of $5 \times 10^5$ dyne/cm$^2$ and higher, substantially about 100% snap back when extended to 1,200% elongation, and a gel rigidity of substantially from about 2 gram to about 1,800 gram Bloom and higher.

More specifically, the gels of the present invention exhibit one or more of the following properties. These are: (1) tensile strength of about $8 \times 10^5$ dyne/cm$^2$ to about $10^7$ dyne/cm$^2$ and greater; (2) elongation of less than about 1,600% to about 3,000% and higher; (3) elasticity modulus of about $10^4$ dyne/cm$^2$ to about $10^6$ dyne/cm$^2$ and greater; (4) shear modulus of about $10^4$ dyne/cm$^2$ to about $10^6$ dyne/cm$^2$ and greater as measured with a 1, 2, and 3 kilogram load at 23° C.; (5) gel rigidity of about less than about 2 gram Bloom to about 1,800 gram Bloom and higher as measured by the gram weight required to depress a gel a distance of 4 mm with a piston having a cross-sectional area of 1 square cm at 23° C.; (6) tear propagation resistance of at least about $5 \times 10^5$ dyne/cm$^2$; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The gel articles molded from the instant compositions have various additional important advantages in that they do not crack, creep, tear, crack, or rupture in flexural, tension, compression, or other deforming conditions of normal use; but rather the molded articles made from the instant composition possess the intrinsic properties of elastic memory enabling the articles to recover and retain its original molded shape after many extreme deformation cycles. In applications where extreme tear resistance, low rigidity, high elongation, good compression set and excellent tensile strength are important, the instant gels would be advantageous.

The gels of the present invention are useful in low frequency vibration applications, such as viscoelastic layers in constrained-layer damping of mechanical structures and goods, as viscoelastic layers used in laminates for isolation of acoustical and mechanical noise, as anti-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components. The compositions are also useful as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. Other uses include various shaped articles as toys, optical uses (e.g. cladding for cushioning optical fibers from bending stresses) and various optical devices, as lint removers, dental floss, as tips for swabs, as fishing bate, as a high vacuum seal (against atmosphere pressure) which contains a useful amount of a mineral oil-based magnetic fluid particles, etc. Moreover, the casted, extruded, or spun threads, strips, yearns, tapes can be weaved into cloths, fine or coarse fabrics.

The instant compositions can be formed in any shape; the original shape can be deformed into another shape (to contact a regular or irregular surface) by pressure and upon removal of the applied pressure, the composition in the deformed shape will recover back to its original shape.

As an example of the versatility of use of the instant gels, a hand exerciser can be made in any shape so long as it is suitable for use as a hand exerciser: a sphere shape, a cube shape, a rectangular shape, etc. Likewise, a wheelchair cushion can be made from the composition in any shape, so long as it meets the needs of the user of the cushion. For example, a cushion can be made by forming th composition into a selected shape matching the contours of the specific body part or body region. The composition can be formed into any desired shaped, size and thickness suitable as a cushion; the shaped composition can be additionally surrounded with film, fabric, foam, or any other desired material or combinations thereof. Moreover, the composition can be casted onto such materials, provided such materials substantially maintain their integrity (shape, appearance, texture, etc.) during the casting process. The same applies for brace cushions for the hand, wrist, finger, forearm, knee, leg, etc.

Other uses include self closing or self tightening enclosures for splicing electrical and telephone cables and wires. For example, the gels can be preformed into a small diameter tubing within an outer elastic tubing, both the internal gel tubing and external elastic tubing can be axially expanded and fixed in place by a removable continuous spiral retainer. Upon insertion of a spliced pair or bundle of cables or wires, the spiral retainer can be removed, as the retainer is removed, the gel and elastic tubing impinges onto the inserted cables or wires splices, thereby sealing the electrical splices against weather, water, dirt, corrosives and shielding the splice from external abuse. The enclosure is completed without the use of heat or flame as is conventionally performed. In the case of multiblock copolymer (I) "treated" gels exhibiting delay recovery or long relaxation times and having extreme tear resistance, a tape of such a gel can be used to wrap the area of a spliced pair or bundle of cable or wire by extending the gel tape and wrapping it around the splice. The delayed recovery of the gel is important in that when the splice is fully wrapped and the gel tape end is let go, it will not quickly unravel itself. This allows time to fix in place an outer elastic shelve around the gel tape wrapped area. Thus, the gel tape will eventually fully recover around the spliced area gradually developing a strong radial recovery force about the spliced area so as to prevent the entry of water, dirt, and other contaminations. Triblock copolymer gels do not have adequate tear strength and have too rapid a recovery to allow time for placement of an outer elastic shelve.

As the treated gels and gels formed from multiblock copolymers (I) having more and more midblock polymer chains can be expected to exhibit greater delay recovery form extension or longer relaxation times with increasing number of midblocks and increasing midblock lengths, such as gels having more than three midblocks forming the copolymers (I) can exhibit extreme tear resistance and excellent tensile strength while at the same time exhibit almost liquid like properties. For example, a fun toy can be made from (S-E-EB-E-S), (S-B-EB-EB-S), (S-E-EP-E-EP-S), (S-P-EB-P-EB-S), (S-E-EB-E-EB-E-S), (S-E-EP-E-EP-E-EP-E-S), (S-E-EP-EP)$_n$, (S-B-EP-E-EP)$_n$, (S-E-EP-E-EP-E)$_n$, (S-E-EB-E-EB-E-EB-E-EB-S)$_n$ copolymer gels which are molded into cube shapes when placed on the surface of a incline will collect it self together and flow down the incline as a moving body much like a volume of water moving on a high surface tension surface. This is due to the greater distance between the end block (A) domains. Such liquid like performing gels can be very strong and exhibit extreme tear resistance as exhibited by gels made from (S-E-EP-S) multiblock copolymer gels with shorter (A) distance between domains. Such liquid like gels when shaped into a cube will be deformed by the force of gravity on Earth, but will retain its memory and regain to its molded cube shape when released in outer space or reform into a cube if let loose in a container of liquid of equal density. As a comparison, such a toy formed in the shape of a large cube from a high viscosity triblock copolymer with a plasticizer content of 1:1,600 parts will be flattened by the force of gravity and run down an incline, but is very fragile and will start to tear if attempt is made to pick it up by hand. This is an excellent comparison of the difference of tear resistance difference between triblock copolymer gels and multiblock copolymer gels. A useful application is to use such an elastic liquid gel volume to fill a container or to encapsulate an electrical or electronic component in a container filling every available space, when needed, the shapeless gel volume can be removed by pouring it out of the container whole.

The most surprising, unexpected, versatile use of the composition is dental flossing. The dental floss can be almost any shape so long as it is suitable for dental flossing. A thick shaped piece of the composition can be stretched into a thin shape and used for flossing. A tinner shaped piece would require less stretching, etc. For purposes of dental flossing, while flossing between two closely adjacent teeth, especially between two adjacent teeth with substantial contact points and more especially between two adjacent teeth with substantial amalgam alloy metal contact points showing no gap between the teeth, it is critical that the gel resist tearing, shearing, and crazing while being stretched to a high degree in such situations. For example, dental gel floss can take the form of a disk where the segments of the circumference of the disk is stretched for flossing between the teeth. Other shaped articles suitable for flossing include threads, strips, yarns, tapes, etc., mentioned above.

In order for gels to be useful as a dental floss, it must overcome the difficult barriers of high shearing and high tearing under extreme elongation and tension loads. The difficulties that the gels must overcome during flossing can be viewed as follows: during the action of flossing, the gel is stretched from no less than about 200% to about 1,100% or higher the gel floss is deformed as it is pulled down with tearing action between the contacting surfaces of the teeth, then, the wedge of gel loss is sheared between the inner contacting surfaces of the teeth, and finally, the elongated wedged of gel floss is pulled upwards and out between the surfaces of the teeth. The forces encountered in the act of flossing are: tension, shearing, tearing under extreme tension.

This invention advances the flossing art by providing strong, soft, and extreme tear resistant gels made from multiblock copolymers which gels are substantially as soft as the gums surrounding the teeth.

Gel floss formed from the gels has many advantages over conventional dental floss such as regular and extra fine waxed and unwaxed nylon floss, spongy nylon fiber floss, and waxed and unwaxed expanded and unexpended teflon floss. Such conventional floss are not recommended for use by children, since a slip or sudden snap in forcing the floss between the teeth may cause injury to the gums which often times results in bleeding. For sensitive gums and inflamed gums which has become red and puffy, it is difficult to floss at, near, and below the gumline. The soft gel floss with softness substantially matching the softness of the gums are of great advantage for use by children and for flossing teeth surrounded by sensitive and tender gums.

The shear resistant characteristics of the gels can be indirectly determined by subjecting the gel to the shear forces of a pair of twisting strings and the resulting inward pulling forces of the twisting strings can be directly read off of a spring scale. As a pair of strings are gradually twisted, typical values will range from less than one pound to fifty pounds and greater. As the string is being twisted (simulating increased shearing forces), the measured pulling forces can range from a low value of 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 . . . to values of 40, 50, 60, 70, 80 pounds and greater.

Gel material of low strength can not resist the tremendous shearing action of the twisting strings. The twisting action of the strings can exhibit a first order twist, a second order twist, or higher order twists. A first order twist refers to one or more twists of a pair of strings (i.e. a pair of strings when twisted together forms a small tight binding helix). A second order twist refers to one or more large binding helixes build up by a par of strings that have been twisted beyond the maximum number of twist which normally produce small tight binding helixes of the first order kind. Similarly, a third order twist refers to a much larger tightly binding helix build up by the maximum number of second order twists produced by the pair of twisting strings. The third order twist may be manifested by the appearance of a branch of two or more twist of the first order twisting strings.

The order of twisting will increase (from a one, two, three, and higher order twist) until the rubber band breaks. Likewise, a looped string with one end attached to a spring scale and the other end attached to a fixed anchor can be twisted into a first, second , third, and higher ordered twist state. This method can be utilized to directly measure the force generated for each ordered twist states. The static force generated by twisting a string on a spring scale is a way of determining the shear force generated in the shearing action of forcing the gel floss between two closely contacting teeth when flossing.

In considering dental flossing criteria, one or more of the following conditions can be regarded as critical factors for dental flossing gels.

Shear Resistant Criteria

For the gels to be considered useful for flossing, the gels, critically, should withstand a twisting string shearing force of at least about 5 Kg, more advantageously at least about 8 Kg, and still more advantageously at least about 10 Kg of inward pulling force of a pair of twisting strings measured directly on a spring scale.

Flossing Cycle Criteria

For the gels to be considered useful for flossing, the gels, critically, should advantageously be able to perform at least 4 flossing cycles, more advantageously 8 cycles, and still more advantageously of about 20 cycles without breaking apart when a 3.0 mm diameter gel strand is tested on a set of simulated upper front teeth fully contacting under a uniform spring load of (0.9027 Kg) two pounds. The simulated upper front teeth comprises two small stainless steel rollers (⅜" dia.) facing lengthwise parallel and forced together so as to form a contact length of ½ inches under a spring load of two pounds as measured by a Entran® model ELO-200-4 load cell adjusted by a straight micrometer at room temperature.

Gel Strength Criteria

For the gels to be considered useful for flossing, the gels, critically, should advantageously exhibit a tensile strength of at least 5 $Kg/cm^2$ (when extended to break as measured at 180° U bend around a 5.0 mm mandrel attached to a spring scale) and more advantageously at least 8 $Kg/cm^2$, and still more advantageously of about 10 $Kg/cm^2$ and higher. The high and gels useful as dental floss can exhibit tensile strengths at break of at least 20 $Kg/cm^2$, more advantageously of at least 40 $Kg/cm^2$, and exceptionally more advantageously at least 60 $Kg/cm^2$. Typically, the tensile strengths range from about 20 $Kg/cm^2$ to about 110 Kg/cm2 and higher, more typically from about 30 $Kg/cm^2$ to 80 $Kg/cm^2$ and higher, especially more typically from about 40 $Kg/cm^2$ to about 90 $Kg/cm^2$ and higher, and exceptionally typically from about 50 $Kg/cm^2$ to about 100 $Kg/cm^2$ and higher.

Propagating Tear Criteria

As a minimum, for the Gels to be considered useful for flossing, the gels, critically, should advantageously exhibit a propagating tear force (when propagating a tear as measured at 180° U bend around a 5.0 mm diameter mandrel attached to a spring scale) of at least about 1 Kg/cm, more advantageously at least 2 Kg/cm, and still more advantageously of about 3 Kg/cm and higher. The gels useful as dental floss can exhibit tear strengths of at least 4 Kg/cm and higher, more advantageously of at least 6 Kg/cm and higher, exceptionally more advantageously of at least 8 Kg/cm and higher. Typically, the tear propagation strength can range from about 5 Kg/cm to about 20 Kg/cm and higher, more typically from about less than 5 Kg/cm to about 25 Kg/cm and higher, especially more typically from about less than 6 Kg/cm to about 30 Kg/cm and higher, and exceptionally more typically from about less than 8 Kg/cm to about 35 Kg/cm and higher.

For the Gels to be considered useful for flossing, the gels, critically, should advantageously exhibit a propagating tension tear force (when a cylindrical sample is notched and a tear is initiated at the notched area and propagated past its maximum cylindrical diameter by length-wise stretching of the cylindrical sample) of at least about 1 Kg/cm, more advantageously at least 2 Kg/cm, and still more advantageously of about 4 Kg/cm and higher. The extreme tear resistant gels typically will exhibit even higher tension tear values.

Rigidity Criteria

The rigidities of the extreme tear resistant useful for flossing can advantageously range from about 350 gram to about 1,800 gram Bloom, more advantageously from about 400 gram to about 1,500 gram Bloom, especially more advantageously from about 450 gram to about 1,200 gram Bloom, still more advantageously from about 450 gram to about 1,000 gram Bloom, and less advantageously at values of greater than 1,800 gram Bloom.

In general, as a minimum, the flossing gels should exhibit several critical properties, including advantageously the ability to:

(1) withstand a shearing force of at least about 5 Kg under the string twisting test described above, (2) perform at least 4 flossing cycles without breaking apart when tested on a set of simulated upper front teeth fully contacting under a uniform spring load of two pound, (3) exhibit a tensile strength of at lest 5 $Kg/cm^2$ and higher, (4) exhibit a propagating tear force at 180° U bend tear test of at least about 1 Kg/cm, and (5) exhibit a propagating tension tear force (on a notched cylindrical sample) of at least about 1 Kg/cm.

For use as a dental floss, the gel is made (by extruding, spinning, casting, etc) as a continuous gel strand, the gel strand can be in the shape of a fiber of a selected diameter (from less than about 0.15 to about 5.0 mm and greater) as a continuous tape having a selected width and thickness (less than 0.10 mm thin to about 5.0 mm and thicker) or in any desired shape suitable for flossing. The fiber, tape or a selected shape is then cut to a desired length, rolled up and placed into a dispenser suitable for containing and dispensing a measured use amount of gel floss. The continuous fiber and tape can be partly cut or notched for measured single or multiple use. When the floss is pulled from the dispenser to a point showing the notched or cut mark on the length of gel floss, the lid is pushed down on the gel floss nipping it and allowing the floss to be further pulled and separated at the notched or cut point. Additionally, a suitable floss dispenser containing a measured length of gel floss can be fitted with a cutting edge attached to its lid or on its body and the uncut and unnotched gel gloss can be dispensed from the dispensing container and cut at the desired measured use length by pressing close the dispenser cutting edge down on the floss so as to nip and cut the gel or by simply closing the dispenser lid or running the gel along the cutting edge on the dispenser body separating a useful length of gel floss.

In practice, typically during flossing, a gel strand will under go various deformations, some of these deformations can be measured, including original shape, extended shape under tension, nipping force, and nipped deformation under a measured force and width. Typically, any shaped gel strand can be used for flossing, a square cross-section, a circular cross-section, a rectangular cross-section, round, oval, etc. For example, a 2.35 mm diameter strand when extended under a force of 2.5 kg can be nipped down to 0.14 mm thickness (along a 3 mm uniform width of its cross-section) by a force of 0.9072 Kg (2.0 pound force), a reduction of 16.78:1; a 1.89 mm diameter strand when extended under a force of 2.5 kg can be nipped down to 0.14 mm thickness by a force of 0.9072 Kg (2.0 pound force), a reduction of 13.5:1; a 2.75 mm diameter strand when extended under a force of 2.5 kg can be nipped down to 0.19 mm thickness by a force of 0.9072 Kg (2.0 pound force), a reduction of 14.4:1; and a 2.63 mm diameter strand when extended under a force of 2.5 kg can be nipped down to 0.19 mm thickness by a force of 0.9072 Kg (2.0 pound force), a reduction of 13.8:1. The cross-section of the gel floss can be reduced to any degree by stretching and nipping (from less than about 1% to about 1,600% and higher). Advantageously, a gel having the required strength, tear resistance, gel rigidity, and other characteristics described can be formed into a floss of any selected cross-section and thickness provided the floss is capable of being stretched when flossing under tension without breaking. Typically the stretching or pulling force is from about less than 0.1 Kg to about 3 Kg and higher. The cross-section of the strand of gel floss should be capable of being nipped by a 0.9027 Kg (2 pounds) force applied across a width of 3 mm from its original cross-sectional dimensions to a nipped thickness of about 3.0 mm to about 0.02 mm and lower, more advantageously from about 2.5 mm to about 0.04 mm and lower, still more advantageously from about 2.0 mm to about 0.08 mm and lower; especially advantageously from about 1.5 mm to about 0.15 mm and lower; especially more advantageously from about 1.2 mm to about 0.20 mm and lower; especially still more advantageously from about 1.0 mm to about 0.25 mm and lower.

The gels made from higher viscosity copolymers (I) are resistant to breaking when sheared than triblock copolymer gels. This can be demonstrated by forming a very soft gel, for example 100 parts copolymer to 800 parts plasticizing oil. The soft gel is cut into a strip of 2.5 cm×2.5 cm cross-section, the gel strip is gripped lengthwise tightly in the left hand about its cross-section and an exposed part of the gel strip being gripped lengthwise around its cross-section tightly by the right hand as close to the left hand as possible without stretching. With the two hands gripping the gel strip's cross-section, the hands are moved in opposite directions to shear apart the gel strip at its cross-section. The shearing action by the gripping hands is done at the fastest speed possible as can be performed by human hands. The shearing action is performed at a fraction of a second, possible at about 0.5 seconds. Using this demonstration, the copolymer (I) gels will not easily break completely apart as would gels formed from triblock copolymers. In some cases, it will take two, three, or more attempts to shear a high viscosity copolymer (I) gel strip this way. Whereas, a lower viscosity triblock copolymer gel trip can be shared apart on the first try. For gels made from copolymers with viscosities of 5 wt % solution in Toluene, their shear resistance will decrease with decreasing viscosity. For example, the shear strengths as tested by hand shearing described above of gels made from copolymers having viscosities of 150, 120, 110, 105, 95, 90, 89, 85, 70, 60, 58, 48, 42, 40, 35, 28, 27, 25, 21 cps, and the like can be expected to decrease with decreasing viscosity.

The tensile strengths of multiblock copolymer gels made from higher viscosity copolymers (I) can be slightly lower than or equal to the tensile strengths of gels made from lower solution viscosity triblock copolymers (II).

Strands of gels comprising higher viscosity multiblock copolymers will perform better than gel strands made from gels of lower viscosity triblock copolymers when used in flossing amalgam molars and more than three times better when used in flossing front teeth.

Gels, in general, will exhibit higher tensile and greater tear resistance than their parent gels containing higher concentrations of plasticizer.

As compared to spongy nylon, regular waxed nylon, and extra fine unwaxed nylon when flossing amalgam molars, the performance of multiblock copolymer gels are on the average substantially better.

While advantageous components and formulation ranges based on the desired properties of the multiblock copolymer gels have been disclosed herein. Persons of skill in the art can extend these ranges using appropriate material according to the principles discussed herein. All such variations and deviations which rely on the teachings through which the present invention has advanced the art are considered to be within the spirit and scope of the present invention.

The invention is further illustrated by means of the following illustrative embodiments, which are given for purpose of illustration only and are not meant to limit the invention to the particular components and amounts disclosed.

Comparisons of oil extended multiblock copolymers have been described in Shell Chemical Company Technical Bulletin SC:1102-89 (April 1989) "KRATON® THERMOPLASTIC RUBBERS IN OIL GELS" which is incorporated herein by reference.

EXAMPLE I

Gels of 100 parts of Kraton G1651, Kuraray Septon 2006 (SEPS), Kurarary Septon 8006 (SEBS), a high viscosity $(SEB)_n$, and a high viscosity $(SEP)_n$ triblock copolymers and 1,600, 1,200, 1,000, 800, 600, 500, 450, and 300 parts by weight of Duraprime 200 white oil are melt blended and samples extruded (from a 7.15 mm diameter orifice) into selected lengths of varying diameters for use as dental floss, the bulk gel rigidities is found to be within the range of 2 to 1,800 gram Bloom, the tensile strength is found to decrease with increase orientation, and the optimum tensile strength found for gel samples with the least amount of stress or orientation imparted during cooling from the molten state to room temperature.

EXAMPLE II

Example I is repeated using Kuraray (S-E-EP-S) 4055 and 4077 multiblock copolymers, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE I. The tensile strength is found to decrease with increase orientation, and the optimum tensile strength found for gel samples with the least amount of stress or orientation imparted during cool from the molten state to room temperature.

EXAMPLE III

Example I is repeated using (S-E-EP-S), (S-E-EP-E-S), (S-B-EP-S), (S-E-EB-S), (S-EB-EP-S), (S-E-EP-EB-S), (S-B-EB-S), (S-E-EB-E-S), (S-B-EP-E-S), (S-B-EB-E-S), (S-B-EP-B-S), (S-B-EB-B-S), (S-E-E-EP-S), (S-E-E-EB-S), (S-B-E-EP-S), (S-B-E-EB-S), (S-B-B-EP-S), (S-B-B-EB-S), (S-E-B-EB-S), (S-E-B-EP-S), (S-EB-EB-S), (S-EP-EP-S), (S-E-EB-EB-S), (S-E-EP-EP-S), (S-E-EB-EP-S), (S-B-EB-EB-S), (S-B-EP-EP-S), (S-B-EB-EP-S), (S-B-EP-EB-S), (S-E-EP-E-EP-S), (S-E-EB-E-EB-S), (S-E-EP-E-EB-S), (S-B-E-EP-B-EP-S), (S-B-EB-B-EB-S), (S-B-EB-B-EP-S), (S-B-EB-E-EB-S), (S-B-EP-E-EP-S), (S-E-EB-B-EP-S), (S-E-EP-B-EB-S), (S-P-EB-S), (S-P-EP-S), (S-P-EP-P-S), (S-P-EB-P-S), (S-B-EP-P-S), (S-B-EB-P-S), (S-P-E-EP-S), (S-P-E-EB-S), (S-B-P-EP-S), (S-B-P-EB-S), (S-P-B-EB-S), (S-P-B-EP-S), (S-P-EB-EB-S), (S-P-EP-EP-S), (S-P-EB-EP-S), (S-P-EP-EB-S), (S-P-EP-P-EP-S), (S-P-EB-P-EB-S), (S-P-EP-P-EB-S), (S-B-EB-P-EB-S), (S-B-EP-P-EP-S), (S-P-EB-B-EP-S), (S-P-EP-B-EB-S), (S-E-EP-P-EP-S), (S-E-EB-P-S), (S-E-P-EP-S), (S-E-P-EB-S), (S-E-EP-P-EP-S), (S-E-EB-P-EB-S), (S-E-EP-P-EB-S), (S-E-EP-E-EP-E-S), (S-B-EP-B-EP-B-S), (S-P-EP-P-EP-P-S), (S-E-EB-E-EB-E-S), (S-P-EP-P-EP-P-S), $(S-E-EP)_n$, $(S-E-EP-E)_n$, $(S-B-EP)_n$, $(S-E-EB-S)_n$, $(S-EB-EP-)_n$, $(S-E-EP-EB)_n$, $(S-B-EB)_n$, $(S-E-EB-E)_n$, $(S-B-EP-E)_n$, $(S-B-EB-E)_n$, $(S-B-EP-B)_n$, $(S-B-EB-B)_n$, $(S-E-E-EP)_n$, $(S-E-E-EB)_n$, $(S-B-E-EP)_n$, $(S-B-E-EB)_n$, $(S-B-B-EP)_n$, $(S-B-B-EB)_n$, $(S-E-B-EB)_n$, $(S-E-B-EP)_n$, $(S-EB-EB)_n$, $(S-EP-EP)_n$, $(S-E-EB-EB)_n$, $(S-E-EP-EP)_n$, $(S-E-EB-EP)_n$, $(S-B-EP-EP)_n$, $(S-B-EB-EP)_n$, $(S-B-EP-EB)_n$, $(S-E-EP-E-EP)_n$, $(S-E-EB-E-EB)_n$, $(S-E-EP-E-EB)_n$, $(S-B-EP-B-EP)_n$, $(S-B-EB-B-EB)_n$, $(S-B-EB-B-EP)_n$, $(S-B-EB-E-EB)_n$, $(S-B-EP-E-EP)_n$, $(S-E-EB-B-EP)_n$, $(S-E-EP-B-EB)_n$, $(S-P-EB)_n$, $(S-P-EP)_n$, $(S-P-EP-P)_n$, $(S-P-EB-P)_n$, $(S-B-EP-P)_n$, $(S-B-EB-P)_n$, $(S-P-E-EP)_n$, $(S-P-E-EB)_n$, $(S-B-P-EP)_n$, $(S-B-P-EB)_n$, $(S-P-B-EB)_n$, $(S-P-B-EP)_n$, $(S-P-EB-EB)_n$, $(S-P-EP-EP)_n$, $(S-P-EB-EP)_n$, $(S-P-EP-EB)_n$, $(S-P-EB-P-EP)_n$, $(S-P-EB-P-EB)_n$, $(S-P-EP-P-EB)_n$, $(S-B-EB-P-EB)_n$, $(S-B-EP-P-EP)_n$, $(S-P-EB-B-EP)_n$, $(S-P-EB-B-EB)_n$, $(S-E-EP-P)_n$, $(S-E-EB-P)_n$, $(S-E-P-EP)_n$, $(S-E-P-EB)_n$, $(S-E-EP-P-EP)_n$, $(S-E-EB-P-EB)_n$, $(S-E-EP-P-EB)_n$, $(S-E-EP-E-EP-E)_n$, $(S-B-EP-B-EP-B)_n$, $(S-P-EP-P-EP-P)_n$, $(S-E-EB-E-EB-E)_n$, and $(S-P-EP-P-EP-P)_n$ multiblock copolymers, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE I. The tensile strength is found to decrease with increase orientation, and the optimum tensile strength found for gel samples with the least amount of stress or orientation imparted during cool from the molten state to room temperature.

EXAMPLE IV

Example II is repeated using plasticizers L-14, L-50, L-100, H-15, H-25, H-35, H-50, H-100, H-300, L-14E, H-300E, Actipol E6, E16, E23, Kraton L-1203, EKP-206, EKP-207, HPVM-2203, Amoco C-60, Piccolyte S10, Duraprime (55, 70, 90, 200, 350, 400), Tufflo (6006, 6016, 6016M, 6026, 6036, 6056, 6206,) Bayol, Bernol, American, Blandol, Drakeol, Ervol, Gloria, and Kaydol, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE I.

EXAMPLE V

Example III is repeated using plasticizers L-14, L-50, L-100, H-15, H-25, H-35, H-50, H-100, H-300, L-14E, H-300E, Actipol E6, E16, E23, Kraton L-1203, EKP-206, EKP-207, HPVM-2203, Amoco C-60, Piccolyte S10, Duraprime (55, 70, 90, 200, 350, 400), Tufflo (6006, 6016, 6016M, 6026, 6036, 6056, 6206,) Bayol, Bernol, American, Blandol, Drakeol, Ervol, Gloria, and Kaydol, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE I.

EXAMPLE VI

A gel composition of 100 parts of Kuraray's S-E-EP-S 4055 copolymer and 400 parts by weight of Duraprime 200 white oil was made following Example I and extruded and drawn (from a 7.15 mm diameter orifice) into a strand of uniform diameter onto a take-up roll of continuous lengths. The strand diameter was varied by increasing and decreasing the speed of the take-up roll. The continuous strand of varying diameter gel strand was cut to suitable lengths for use and testing as dental floss. Additional gel was also casted in varying thickness and tested. The results of samples tested are shown in Table 1B, #4–7,; Table 2, #12–15 and 20; Table 3 #22, 23, 27–29; Table 4 #36–32; Table 5, #40–43, #76 and 77. Samples Nos. 76 and 77 were tested together. Sample 77 exhibited higher tensile strength after 27.75% of plasticizing oil was extracted (with 2.89 parts by weight of oil remaining), its rigidity remained substantially unchanged.

EXAMPLE VII

A gel composition of 100 parts of Kraton G1651 and 400 parts by weight of Duraprime 200 white oil was made following Example I and extruded and drawn (from a 7.15 mm diameter orifice) into a strand of uniform diameter onto a take-up roll of continuous lengths. The strand diameter was varied by increasing and decreasing the speed of the take-up roll. The continuous strand of varying diameter gel strand was cut to suitable lengths for use and testing as dental floss. Additional gel was also casted in varying thickness and tested. The results of samples tested are shown in Table 1B, #8–11; Table 2, #16–19 and 21; Table 3, #24–26; Table 4, #33–35; and Table 5, #36–39.

EXAMPLE VIII

Example II was repeated melt blending under inert gas 100 parts by weight of Kuraray (S-E-EP-S) 4077 multiblock copolymer and 400 parts by weight of Duraprime 70 white oil. A first part of the molten gel was allowed to cool to room temperature, the remainder gel was heated under inert gas for an additional three hours at 300–325° F. and a second part of the gel was extruded (from a 7.15 mm diameter orifice) into cold running water, and the third and final remaining gel was allowed to cool to room temperature. The bulk gel rigidities of the first, second and third parts were found to be within the range of 2 to 1,800 gram Bloom. The second and third final parts of the gel appeared to be altered and different from the first gel part. The first part exhibited rapid return when extended, but the second and third final parts exhibited delay elastomeric recovery when released after extension and deformation. All of the samples exhibited 100% recovery after repeated extensions and deformations.

TABLE 1A

Flossing Cycles to Break

| Sample No. | Floss Type | cross-section size (mm$^2$) | [2]Floss amalgam molars to break | [3]Floss fronts to break |
|---|---|---|---|---|
| 1 | [4]Unwaxed spongy nylon | 0.30 | 18 | 200+ |
| 2 | [5]Regular waxed nylon | 0.11 | 11 | 200+ |
| 3 | [6]Extra fine unwaxed nylon | 0.06 | 6 | 200+ |

TABLE 1B

Flossing Cycles to Break

| Sample No. | Floss Type | [1]Relaxed/extended dia. (mm) | [2]Floss amalgam molars to break | [3]Floss fronts to break |
|---|---|---|---|---|
| 4 | [7]Gel | 2.42/0.16 | 37 | 76 |
| 5 | [7]Gel | 2.63/0.17 | 29 | 83 |
| 6 | [7]Gel | 2.75/0.17 | 36 | 183 |
| 7 | [7]Gel | 2.83/0.20 | 20 | 74 |
| 8 | [8]Gel | 3.22/0.22 | 8 | 30 |
| 9 | [8]Gel | 2.48/0.31 | 4 | 20 |
| 10 | [8]Gel | 3.16/0.33 | 6 | 44 |
| 11 | [8]Gel | 2.86/0.24 | 5 | 29 |

[1]floss dimension relaxed state and when extended during flossing cycles.
[2]Test conditions: number of flossing cycles (before breaking) between amalgam alloy metal (fully contacting) lower, left first and second human back molars.
[3]Test conditons: number of flossing cycles (before breaking) between upper human front teeth.
[4]Oral-B Ultra Floss ™, interlocking network of spongy nylon floss.
[5]Johnson & Johnson regular waxed nylon floss.

TABLE 1B-continued

Flossing Cycles to Break

| Sample No. | Floss Type | [1]Relaxed/extended dia. (mm) | [2]Floss amalgam molars to break | [3]Floss fronts to break |
|---|---|---|---|---|

[6]Johnson & Johnson extra fine unwaxed nylon floss.
[7]Gel made from 100 parts by weight of S-E-EP-S 4055 multiblock copolymer having a Brookfield viscosity of 90 as measured for a 5 wt % solution in toluene at 30° C. and 400 parts by weight of Duraprime 200 plasticizing oil.
[8]Gel made from 100 parts by weight of SEBS Kraton G1651 copolymer having a Brookfield viscosity of 40 as measured for a 5 wt % solution in toluene at 30° C.
[2,3]Any selected test methods may be utilized in testing the floss performance of the gels. For example, a set of simulated upper front teeth fully contacting under a uniform spring load of two pounds may be used in place of human teeth. Such simulated testing conditions may be more severe than conditions 2 and less severe than conditions 3 above.

TABLE 2

Tensile Strength of Gel Strands

| Sample No. | Number of Strands | Radius (mm) | Area (cm$^2$) | Failure (Kg) | Tensile (Kg/cm$^2$) |
|---|---|---|---|---|---|
| 12 | 3 | 1.325 | 0.165 | 9.00 | 54.54 |
| 13 | 4 | 1.250 | 0.196 | 9.50 | 48.39 |
| 14 | 4 | 1.421 | 0.253 | 9.50 | 37.44 |
| 15 | 5 | 1.359 | 0.290 | 12.5 | 43.08 |
| 16 | 2 | 2.14 | 0.287 | 14.0 | 48.78 |
| 17 | 2 | 1.55 | 0.151 | 11.5 | 75.95 |
| 18 | 2 | 1.17 | 0.086 | 8.50 | 98.84 |
| 19 | 2 | 1.322 | 0.109 | 9.0 | 81.96 |
| 20 | 6 | 1.375 | 0.356 | 14 | 39.32 |
| 21 | 2 | 1.445 | 0.131 | 10 | 76.33 |
| 76 | 1 | 1.22 | 0.0467 | 2.00 | 42.82 |
| 77† | 1 | 1.38 | 0.0598 | 4.00 | 66.88 |

†Plasticizing oil extracted

TABLE 3

Tensile Strength of Bulk Gels Samples

| Sample No. | Cross-section (cm2) | Failure (Kg) | Tensile (Kg/cm2) |
|---|---|---|---|
| 22 | 1.96 | 24.0 | 12.24 |
| 23 | 1.56 | 25.0 | 16.02 |
| 24 | 0.58 | 15.0 | 25.83 |
| 25 | 0.602 | 16.0 | 26.54 |
| 26 | 1.163 | 24.0 | 20.64 |
| 27 | 0.913 | 21.0 | 23.00 |
| 28 | 0.595 | 18.5 | 36.56 |
| 29 | 0.702 | 19.0 | 27.06 |

TABLE 4

180° U Bend Tear Propagation of Bulk Gels Samples

| Sample No. | Tear width (cm) | Failure (Kg) | Tear Force (Kg/cm) |
|---|---|---|---|
| 30 | 1.31 | 2.75 | 2.09 |
| 31 | 1.28 | 3.0 | 2.30 |
| 32 | 1.14 | 2.75 | 2.56 |
| 33 | 1.53 | 2.75 | 1.79 |
| 34 | 1.27 | 2.25 | 1.76 |
| 35 | 1.26 | 2.25 | 1.77 |

TABLE 5

Notched Gel Strand Tension Tear Propagation

| Sample No. | Strand Dia. (mm) | Failure (Kg) | Tear Force (Kg/cm) |
|---|---|---|---|
| 36 | 2.86 | 0.75 | 2.62 |
| 37 | 2.49 | 0.75 | 3.01 |
| 38 | 3.09 | 0.60 | 1.94 |
| 39 | 2.62 | 0.70 | 2.67 |
| 40 | 2.54 | 0.60 | 2.36 |
| 41 | 1.94 | 1.10 | 5.67 |
| 42 | 1.58 | 0.75 | 4.74 |
| 43 | 2.34 | 1.2 | 5.12 |

The tensile strengths of gels made from higher viscosity copolymers are lower than the tensile strengths of gels made from lower solution viscosity copolymers. This was later found to be due to orientation effects and not considered significant.

The tear resistance of gels made from higher viscosity copolymers are higher than the tear resistance of gels made from lower solution viscosity copolymers.

Gel strands made from higher viscosity copolymers perform better than gel strands made of lower viscosity copolymers when used in flossing amalgam molars and more than three times better when used in flossing front teeth.

As compared to spongy nylon, regular waxed nylon, and extra fine unwaxed nylon when flossing amalgam molars, the performance of gels are on the average substantially better.

Examples below illustrate other modes of practice contemplated.

EXAMPLE VIII

At least 120 pcs of the gel strands of EXAMPLE II containing 600 parts oil is individually weighted and placed in a heated vacuum oven, a partial vacuum is applied and the temperature is regulated between about 80° F. to about 150° F. to extract plasticizer from the gel strands. At various oven and vacuum times, three gel strands are removed from the vacuum oven, allowed to cool to room temperature, weighted to determine the amount of weight loss and tested for tensile and tear strength. As the amount of oil contained in the original gel is reduced from 600 parts by weight to less than 200 parts by weight, the "reduced plasticizer volume" gels are weighted and tested. The tear and tensile strengths of the reduced plasticizer volume gels are found to be improved over the properties of the original 600 parts by weight referenced gel strands.

The gels are especially advantageously useful when subjected to conditions of stretching, shearing, and tearing during flossing. The gels useful for flossing are characterized by low rigidities and high solution viscosity of the gels made from multiblock copolymers having two or more midblock polymer chains.

Tables 6–9 are illustrative in meeting one or more of the criteria detailed above.

TABLE 6

Illustrative Modes of Practice Contemplated for multiblock copolymer Gels

| 100 Parts by wt | 5 Wt % Copolymer Viscosity (cps) | Styrene % | Parts by Wt of Oil | Number of floss cycles to break | Sample No. |
|---|---|---|---|---|---|
| S-E-EP-S | 90 | 30 | 300 | 30+ | 44 |
| S-E-EP-E-S | 60 | 30 | 300 | 30+ | 45 |
| (S-E-EP)n | 240 | 35 | 300 | 30+ | 46 |
| (S-E-EP-E)n | 240 | 35 | 300 | 30+ | 47 |
| S-B-EP-S | 90 | 30 | 300 | 30+ | 48 |
| S-E-EB-S | 90 | 35 | 300 | 30+ | 49 |
| S-EB-EP-S | 90 | 30 | 300 | 30+ | 50 |
| S-E-EP-EP-S | 90 | 30 | 300 | 30+ | 51 |

TABLE 7

Illustrative Modes of Practice Contemplated for multiblock copolymer Gels

| 100 Parts by wt | 5 Wt % Copolymer Viscosity (cps) | Styrene % | Parts by Wt of Oil | Number Floss cycles to Break | Sample No. |
|---|---|---|---|---|---|
| S-E-EP-EB-S | 120 | 33 | 250 | 30+ | 52 |
| S-E-EP-EP-S | 120 | 33 | 250 | 30+ | 53 |
| (S-B-EP)n | 380 | 35 | 250 | 30+ | 54 |
| (S-E-EB)n | 380 | 35 | 250 | 30+ | 55 |
| S-E-EP-E-EP-S | 120 | 30 | 250 | 30+ | 56 |
| S-E-EP-P-S | 120 | 35 | 250 | 30+ | 57 |
| S-E-B-EP-S | 120 | 30 | 250 | 30+ | 58 |
| S-E-EP-EP-E-S | 120 | 30 | 250 | 30+ | 59 |

TABLE 8

Illustrative Modes of Practice Contemplated for multiblock copolymer (0.5–2.0 cm diameters) Gel Strands

| 100 Parts by wt | 5 Wt % Copolymer Viscosity (cps) | Styrene % | Parts by Wt of Oil | # Floss cycles to Break | Sample No. |
|---|---|---|---|---|---|
| S-E-EP-S | 40 | 30 | 350 | 30+ | 60 |
| S-E-EP-S | 60 | 30 | 350 | 30+ | 61 |
| (S-E-EP-EB)n | 340 | 30 | 350 | 30+ | 62 |
| (S-E-EP-EP-E)n | 340 | 30 | 350 | 30+ | 63 |
| S-E-EP-E-EP-E-S | 90 | 30 | 350 | 30+ | 64 |
| S-EB-EP-EP-S | 90 | 35 | 350 | 30+ | 65 |
| S-B-EB-B-S | 90 | 30 | 350 | 30+ | 66 |
| S-E-EP-EP-E-S | 90 | 30 | 350 | 30+ | 67 |

TABLE 9

Illustrative Modes of Practice Contemplated for multiblock copolymer (0.5–2.0 cm diameters) Gel Strands

| 100 Parts by wt | 5 Wt % Copolymer Viscosity (cps) | Styrene % | Parts by Wt of Oil | # Floss cycles to Break | Sample No. |
|---|---|---|---|---|---|
| S-E-EB-S | 120 | 30 | 250 | 40+ | 68 |
| S-E-EP-S | 120 | 30 | 250 | 40+ | 69 |
| (S-E-EB)n | 280 | 35 | 250 | 40+ | 70 |
| (S-E-EP)n | 280 | 35 | 250 | 40+ | 71 |
| S-E-EP-E-S | 120 | 30 | 250 | 40+ | 72 |
| S-EP-E-EP-S | 120 | 30 | 250 | 40+ | 73 |
| S-EB-E-EB-S | 120 | 30 | 250 | 40+ | 74 |
| S-EB-EB-S | 120 | 30 | 250 | 40+ | 75 |

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims.

What I claim is:

1. A gel composite comprising:
   (i) one or more of a poly(ethylene) crystallite forming linear or star-shaped multiblock copolymers with glassy polymer end blocks or a mixture of two or more of said copolymers; said copolymers having two or more midblock polymer chains and
   (ii) a selected amount of a plasticizing oil;
   (iii) said gel, denoted by G, is physically interlocked with a selected material M forming said gel composite of the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, or a permutation of one or more of said $G_n$ with $M_n$, wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity; said gel characterized by a gel rigidity of from about 2 gram to about 1,800 gram Bloom; wherein said gel is capable of exhibiting greater tear propagation resistance than a gel having a corresponding rigidity made from poly(styrene-ethylene-butylene-styrene) or poly(styrene-ethylene-propylene-styrene) block copolymers having substantially non-crystallite forming poly(ethylene) midblocks.

2. A gel composite comprising:
   (i) 100 parts by weight of one or more of a crystalline linear or star-shaped multiblock copolymers or a mixture of two or more of said copolymers; said gel characterized by a gel rigidity of from about 2 gram to about 1,800 gram Bloom; said linear multiblock copolymer have the general configuration A—Z—A and said star-shaped multiblock copolymer have the general configuration $(A—Z)_n$, the subscript n is an integer; wherein each A is a selected glassy polymer end block segment of polystyrene and wherein Z is a midblock of one or more polymer chains of crystallite forming poly(ethylene) in combination with one or more polymer chains of poly(ethylene-butylene) or poly(ethylene-propylene); and
   (ii) a selected amount of a plasticizing oil;
   (iii) said gel, denoted by G, is physically interlocked with a selected material M forming said gel composite of the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, or a permutation of one or more of said $G_n$ with $M_n$, wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity; wherein said gel is capable of exhibiting greater tear propagation resistance than a gel having a corresponding rigidity made from poly(styreneethylene-butylene-styrene) or poly(styrene-ethylene-propylene-styrene) block copolymers having substantially non-crystallite forming poly(ethylene) midblocks.

3. A gel composite comprising:
(i) 100 parts by weight of one or more of a crystalline linear multiblock copolymers or a mixture of two or more of said copolymers; said gel characterized by a gel rigidity of from about 2 gram to about 1,800 gram Bloom; said linear multiblock copolymer have the general configuration A—Z—A; wherein each A is a selected glassy polymer end block segment of polystyrene and wherein Z is a midblock of one or more polymer chains of crystallite forming poly(ethylene) in combination with one or more polymer chains of poly(ethylene-butylene) or poly(ethylene-propylene); and
(ii) a selected amount of a plasticizing oil;
(iii) said gel, denoted by G, is physically interlocked with a selected material M forming said gel composite of the combination $G_nM_n$, $G_nM_nG_n$, $M_nG_nM_n$, or a permutation of one or more of said $G_n$ with $M_n$, wherein when n is a subscript of M, n is the same or different selected from the group consisting of foam, fabric, or synthetic fibers; and wherein when n is a subscript of G, n denotes the same or a different gel rigidity; wherein said gel is capable of exhibiting greater tear propagation resistance than a gel having a corresponding rigidity made from poly(styrene-ethylene-butylene-styrene) or poly(styrene-ethylene-propylene-styrene) block copolymers having substantially non-crystallite forming poly(ethylene) midblocks.

4. A gel composite comprising:
(i) 100 parts by weight of one or more of a crystalline star-shaped multiblock copolymers or a mixture of two or more of said copolymers; said gel characterized by a gel rigidity of from about 2 gram to about 1,800 gram Bloom; said star-shaped multiblock copolymer have the general configuration $(A—Z)_n$, the subscript n is an integer; wherein each A is a selected glassy polymer end block segment of polystyrene and wherein Z is a midblock of one or more polymer chains of crystallite forming poly(ethylene) in combination with one or more polymer chains of poly(ethylene-butylene) or poly(ethylene-propylene); and
(ii) a selected amount of a plasticizing oil;
(iii) said gel, denoted by G, is physically interlocked with a selected material M forming said gel composite of the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$ or a permutation of one or more of said $G_n$ with $M_n$, wherein when n is a subscript of M, n is the same or different selected from the group consisting of foam, plastic, fabric, metal, or synthetic resin, synthetic fibers; and wherein when n is a subscript of G, n denotes the same or a different gel rigidity; wherein said gel is capable of exhibiting greater tear propagation resistance than a gel having a corresponding rigidity made from poly (styrene-ethylene-butylene-styrene) or poly(styrene-ethylene-propylene-styrene) block copolymers having substantially non-crystallite forming poly(ethylene) midblocks.

5. A gel composite according to claim 2, wherein said gel is being denoted by G, is physically interlocked with a selected material M forming the combination $G_nM_n$, $G_nM_nG_n$, $M_nG_nM_n$, $M_nG_nG_nM_n$, $G_nM_nM_nG_n$, $G_nM_nG_nM_nG_n$, or a permutation of one or more of said $G_n$ with $M_n$, wherein when n is a subscript of M, n is the same or different selected from the group consisting of a fabric, a fiber, or a film; and wherein when n is a subscript of G, n denotes the same or a different gel rigidity.

6. A gel composite according to claim 1, wherein said multiblock copolymer is poly(styrene-ethylene-ethylene-propylene-styrene) or poly(styrene-ethylene-ethylene-butylene-styrene), and said tear propagation resistance is measured using a 180° U bend tear propagation test.

7. A gel composite according to claim 2, wherein said multiblock copolymer is poly(styrene-ethylene-ethylene-propylene-styrene), poly(styrene-ethylene-ethylene-butylene-styrene), poly(styrene-ethylene-ethylene-propylene)$_n$, and poly(styrene-ethylene-ethylene-butylene)$_n$; and said tear propagation resistance is determined by repeatedly inserting a 3.0 mm diameter gel strand held in position under a tensile force of 1 Kg/cm$^2$ between two stainless steel rollers (⅜ inches diameter) facing lengthwise parallel and forced together so as to form a contact length of ½ inches under a spring load of two pounds.

8. A gel composite according to claim 2, wherein said gel is formed with a selected amount of one or more selected polymer or copolymer selected from the group consisting of poly(styrene-butadiene-styrene), poly(styrene-butadiene), poly(styrene-isoprene-styrene), poly(styrene-isoprene), poly(styrene-ethylene-propylene), poly(styrene-ethylene-propylene-styrene), poly(styrene-ethylene-butylene-styrene), poly(styrene-ethylene-butylene), poly(styrene-ethylene-propylene)n, poly(styrene-ethylene-butylene)n, polystyrene, polybutylene, poly(ethylene-propylene), poly(ethylene-butylene), polypropylene, or polyethylene, wherein said selected copolymer is a linear, branched or star-shaped, or multiarm copolymer.

9. A gel composite according to claim 2, wherein said copolymer is a linear multiblock copolymers of the formula poly(styrene-ethylene-ethylene-propylene-styrene), poly(styrene-ethylene-ethylene-butylene-styrene), poly(styrene-ethylene-ethylene-propylene-ethylene-butylene-styrene), poly(styrene-ethylene-ethylene-propylene-ethylene-styrene), and poly(styrene-ethylene-ethylene-propylene-ethylene-ethylene-propylene-ethylene-styrene).

10. A gel composite according to claim 2, wherein said star-shaped multiblock copolymers is of the formula poly(styrene-ethylene-ethylene-butylene)$_n$, poly(styrene-ethylene-ethylene-propylene)$_n$, poly(styrene-ethylene-ethylene-propylene-ethylene)$_n$, poly(styrene-ethylene-ethylene-propylene-ethylene-ethylene-propylene)$_n$, and poly(styrene-ethylene-ethylene-propylene-ethylene-ethylene-propylene-ethylene)$_n$.

11. A gel composite according to claim 2, wherein said gel, denoted by G, is physically interlocked with a selected material M forming a composite of the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, or a permutation of one or more of said $G_n$ with $M_n$, wherein when n is a subscript of M, n M, n is the same or different selected from the group consisting of foam, plastic, fabric, metal, synthetic resin, or synthetic fibers; and wherein when n is a subscript of G, n denotes the same or a different gel rigidity of from about 2 gram to about 1,800 gram Bloom.

12. A gel composite comprising:
(i) 100 parts by weight of one or more of a crystalline linear or star-shaped multiblock copolymers or a mixture of two or more of said copolymers; said gel characterized by a gel rigidity of from about 2 gram to about 1,800 gram Bloom; said linear multiblock copolymer have the general configuration A—Z—A and said star-shaped multiblock copolymer have the general configuration $(A—Z)_n$, the subscript n is an integer; wherein each A is a selected glassy polymer end block segment of polystyrene, poly(alpha-methylstyrene), poly(o-methylstyrene), poly(m-methylstryene), poly(p-methylstyrene) or poly(tertiary-butylstyrene) and wherein Z is a midblock of one or more polymer chains of crystallite forming poly (ethylene) in combination with one or more polymer chains of poly(ethylene-butylene) or poly(ethylene-propylene); and (ii) a selected amount of a plasticizing oil; wherein said gel is capable of exhibiting greater tear resistance than a gel having a corresponding rigidity made from poly (styrene-ethylene-butylene-styrene) or poly(styrene-ethylene-propylene-styrene) block copolymers having substantially non-crystallite forming poly(ethylene) midblocks; and wherein said gel, denoted by G, is physically interlocked with a selected material M forming a composite of the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nM_n$, $G_nM_nG_nM_nM_n$, $M_nG_nM_nG_nM_n$, $G_nG_nM_nM_nG_n$, $G_nG_nM_nG_nM_nG_n$, or a permutation of one or more of said $G_n$ with $M_n$, wherein when n is a subscript of M, n is the same or different selected from the group consisting of foam, plastic, fabric, or synthetic fibers; and wherein when n is a subscript of G, n denotes the same or a different gel rigidity of from about 2 gram to about 1,800 gram Bloom.

13. A gel composite according to claims 1, wherein said glassy polymer end blocks is polystyrene, said composite combination is $G_nM_n$, and said M is foam, fabric, or synthetic fibers.

14. A gel composite according to claims 1, wherein said glassy polymer end blocks is polystyrene, said composite combination is $G_nM_n$, $G_nM_nG_n$, or a permutation of one or more of said $G_n$ with $M_n$, wherein M is foam, fabric, or synthetic fibers.

15. A gel composite comprising:

(i) 100 parts by weight of one or more of a crystalline linear or star-shaped multiblock copolymers or a mixture of two or more of said copolymers; and (ii) a selected amount of a plasticizing oil;

(iii) said gel, denoted by G, is physically interlocked with a selected material M forming said gel composite of the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, or a permutation of one or more of said $G_n$ with $M_n$, wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity; said gel characterized by a gel rigidity of from about 2 gram to about 1,800 gram Bloom; said linear multiblock copolymer have the general configuration A—Z—A and said star-shaped multiblock copolymer have the general configuration $(A—Z)_n$, the subscript n is an integer; wherein each A is a selected glassy polymer end block segment of polystyrene, poly(alpha-methylstyrene), poly(o-methylstyrene), poly(m-methylstryene), poly(p-methylstyrene) or poly(tertiary-butylstyrene) and wherein Z is a midblock of one or more polymer chains of crystallite forming poly (ethylene) in combination with one or more polymer chains of poly(ethylene-butylene) or poly(ethylene-propylene); wherein said linear multiblock copolymers having a solution viscosity at 5 weight percent solution in toluene at 30° C. of at least 150 cps and said star-shaped multiblock copolymers having a solution viscosity at 5 weight percent solution in toluene at 30° C. of a least 200 cps; said gel upon heat treatment for a selected temperatures and time period exhibits delay deformation recovery and greater tear resistance than a gel having a corresponding rigidity made from poly (styrene-ethylene-butylene-styrene) or poly(styrene-ethylene-propylene-styrene) block copolymers having substantially non-crystallite forming poly(ethylene) midblocks.

16. A composite according to claims 1, wherein said glassy polymer end blocks is polystyrene, said composite combination is $G_nM_n$, $G_nM_nG_n$, $M_nG_nM_n$ or a permutation of one or more of said $G_n$ with $M_n$, wherein M is foam, fabric, or synthetic fibers.

17. A composite according to claims 1, wherein said glassy polymer end blocks is polystyrene, said composite combination is $G_nM_n$, $G_nM_nG_n$, $M_nG_nM_n$, $G_nG_nM_n$ or a permutation of one or more of said $G_n$ with $M_n$, wherein M is foam, fabric, or synthetic fibers.

18. A composite according to claims 1, wherein said glassy polymer end blocks is polystyrene, said composite combination is $G_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, or a permutation of one or more of said $G_n$ with $M_n$, wherein M is foam, fabric, or synthetic fibers.

19. A gel composite according to claim 2 wherein said gel composite of said gel and said fibers being extruded into a thread or tape and weaved into a fine or coarse fabric article.

20. A gel composite according to claim 2, wherein said gel being formed into a shape floss suitable for use as a dental floss in combination with or without one or more selected polymers or copolymers of polybutylene, polypropylene, or polyethylene.

* * * * *